United States Patent
Randall et al.

(10) Patent No.: US 7,304,084 B2
(45) Date of Patent: Dec. 4, 2007

(54) 6-[(4,5-DIHYDRO-1H-IMIDAZOL-2-YL) AMINO]-7-METHYL-1H-BENZIMIDAZOLE-4-CARBONITRILE AND ITS PREFERRED SALT

(75) Inventors: Jared Lynn Randall, Smyrna, NY (US); Richard Alan Gibbs, Norwich, NY (US); Gregory Kent Bosch, West Chester, OH (US); Michael David Curtis, Norwich, NY (US); Li Sun, Grays Lake, IL (US); Nicholas Nikolaides, Mason, OH (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 11/332,998

(22) Filed: Jan. 17, 2006

(65) Prior Publication Data

US 2006/0122248 A1    Jun. 8, 2006

Related U.S. Application Data

(62) Division of application No. 10/386,958, filed on Mar. 12, 2003, now abandoned.

(60) Provisional application No. 60/448,811, filed on Feb. 20, 2003.

(51) Int. Cl.
*A61K 31/4181* (2006.01)
(52) U.S. Cl. ...................................... 514/388
(58) Field of Classification Search ................. 514/388
See application file for complete search history.

(56) References Cited

U.S. PATENT DOCUMENTS

| | | |
|---|---|---|
| 5,478,858 A | 12/1995 | Cupps et al. |
| 5,541,210 A | 7/1996 | Cupps et al. |
| 5,691,370 A | 11/1997 | Cupps et al. |
| 6,066,740 A | 5/2000 | Godlewski et al. |

FOREIGN PATENT DOCUMENTS

| | | |
|---|---|---|
| WO | WO 95/16685 | 6/1995 |
| WO | WO 96/04270 | 2/1996 |
| WO | WO 98/23595 | 6/1998 |
| WO | WO 98/46595 | 10/1998 |
| WO | WO 99/26942 | 6/1999 |

*Primary Examiner*—Taofiq Solola
(74) *Attorney, Agent, or Firm*—Greenlee, Winner, and Sullivan, P.C.

(57) ABSTRACT

6-[(4,5-Dihydro-1H-imidazol-2-yl)amino-]-7-methyl-1H-benzimidazole-4-carbonitrile substantially free of 2,3,7-tri-amino-4,6-dimethyl-1,9-phenazinedicarbonitrile, and the anhydrous monoacetate salt thereof, are useful in the treatment of alpha-2 mediated disorders such as ocular hypertension.

4 Claims, No Drawings

6-[(4,5-DIHYDRO-1H-IMIDAZOL-2-YL) AMINO]-7-METHYL-1H-BENZIMIDAZOLE-4-CARBONITRILE AND ITS PREFERRED SALT

CROSS REFERENCE TO RELATED APPLICATION

This application is a divisional application of U.S. application Ser. No. 10/386,958 filed Mar. 12, 2003 now abandoned, which claims the benefit of U.S. Provisional Application No. 60/448,811 filed Feb. 20, 2003. Priority is hereby claimed to each of these applications. The subject matter of each of these applications is hereby incorporated.

FIELD OF THE INVENTION

The present invention relates to chemical processes for making 6-[(4,5-Dihydro-1H-imidazol-2-yl)amino-]-7-methyl-1H-benzimidazole-4-carbonitrile and its preferred salt form, the anhydrous monoacetate salt.

BACKGROUND OF THE INVENTION

6-[(4,5-Dihydro-1H-imidazol-2-yl)amino-]-7-methyl-1H-benzimidazole-4-carbonitrile is a selective alpha-2 receptor agonist that may be useful for the treatment of various alpha-2 mediated disorders. These disorders include, but are not limited to, irritable bowel syndrome, migraine, chronic tension type headache, ocular hypertension, muscle spasm, muscle hypertonia, attention deficit hyperactivity disorder, sedation, adjunct for anesthesia, anxiety, and Tourette's Syndrome.

The present invention relates to chemical processes suitable for large scale synthesis for making 6-[(4,5-Dihydro-1H-imidazol-2-yl)amino-]-7-methyl-1H-benzimidazole-4-carbonitrile and its preferred anhydrous monoacetate salt. Although the synthesis of 5-(2-imidazolinylamino)-benzimidazoles is generally described, for example, in International Publications WO 95/16685, WO 96/0427, and U.S. Pat. No. 6,066,740, there are many disadvantages in the syntheses described. The most pronounced disadvantage to these previously described methods, is the generation and failure to identify a highly mutagenic side product of the phenazine class of molecules. These previous methods also describe salt forms of 6-[(4,5-Dihydro-1H-imidazol-2-yl)amino-]-7-methyl-1H-benzimidazole-4-carbonitrile that exhibit low water solubility, a property that is undesirable for formulation and absorption from the gastrointestinal tract.

In view of the foregoing, there is a need for a synthesis method for 6-[(4,5-Dihydro-1H-imidazol-2-yl)amino-]-7-methyl-1H-benzimidazole-4-carbonitrile that significantly reduces the occurrence of the phenazine impurity and a salt form of 6-[(4,5-Dihydro-1H-imidazol-2-yl)amino-]-7-methyl-1H-benzimidazole-4-carbonitrile that exhibits enhanced water solubility.

SUMMARY OF THE INVENTION

The present invention meets these needs by providing methods of making 6-[(4,5-Dihydro-1H-imidazol-2-yl)amino-]-7-methyl-1H-benzimidazole-4-carbonitrile, or a tautomer thereof, substantially free of highly mutagenic phenazine derivatives, as well as an anhydrous, monoacetate salt form of 6-[(4,5-Dihydro-1H-imidazol-2-yl)amino-]-7-methyl-1H-benzimidazole-4-carbonitrile that exhibits enhanced water solubility.

More specifically, one aspect of the invention provides for a composition of 6-[(4,5-Dihydro-1H-imidazol-2-yl) amino-]-7-methyl-1H-benzimidazole-4-carbonitrile substantially free of the novel phenazine chemical entity 2,3,7-triamino-4,6-dimethyl-1,9-phenazinedicarbdnitrile. Pharmaceutical compositions comprising, and methods of treating alpha-2 mediated disorders using said 6-[(4,5-Dihydro-1H-imidazol-2-yl)amino-]-7-methyl-1H-benzimidazole-4-carbonitrile are also provided.

Another aspect of the invention provides for a method of making a preferred intermediate in the synthesis of 6-[(4,5-Dihydro-1H-imidazol-2-yl)amino-]-7-methyl-1H-benzimidazole-4-carbonitrile of formula (II):

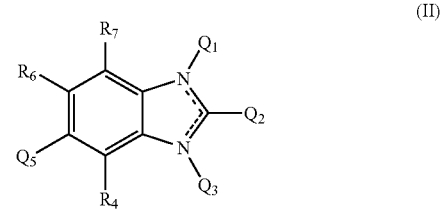

wherein:
(a) $Q_1$, and $Q_3$ are each independently selected from the group consisting of hydrogen, hydrogen functional group equivalent, and nil;
(b) $Q_2$ is selected from hydrogen or hydrogen functional group equivalent;
(c) $R_4$ is selected from the group consisting of amide, carboxylic acid, cyano, carboxylic acid functional group equivalent, and cyano functional group equivalent;
(d) $Q_5$ is selected from hydrogen or hydrogen functional group equivalent;
(e) $R_6$ is selected from the group consisting of amino, nitro, formylamino, and amino functional group equivalent; and
(f) $R_7$ is selected from methyl or methyl functional group equivalent;
(g) or tautomer thereof;

comprising:
a) providing a compound of formula (I):

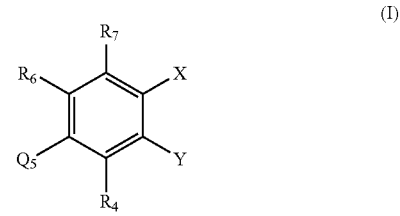

wherein:
  (a) X and Y are each independently selected from the group consisting of nitro, amino, formylamino, nitrogen/one carbon equivalent conjugate, and amino functional group equivalent;
  (b) $R_4$ is selected from the group consisting of carboxylic acid, cyano, carboxylic acid functional group equivalent, and cyano functional group equivalent;
  (c) $Q_5$ is selected from hydrogen or hydrogen functional group equivalent;
  (d) $R_6$ is selected from the group consisting of hydrogen, amino, nitro, and amino functional group equivalent;
  (e) $R_7$ is selected from methyl or methyl functional group equivalent;
  (f) provided X and Y are not both amino; and
  (g) provided X and Y are not both nitrogen/one carbon equivalent conjugate;
  b) cyclizing the formula (I) compound in a single pot by using a nonferrous metal hydrogenation catalyst, in the presence of hydrogen or a hydrogen donor, and optionally a cyclization agent, yielding the compound of formula (II). A cyclization agent may be optionally used when X or Y in formula (I) is not a nitrogen/one carbon equivalent conjugate.

One aspect of the invention provides for a method of making a formula (II) intermediate substantially free of a phenazine of formula (III):

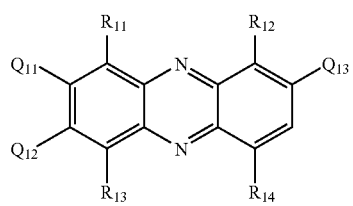

(III)

wherein:
  (a) $Q_{11}$, $Q_{12}$ and $Q_{13}$ are each independently selected from the group consisting of nitro, amino, formylamino, and amino functional group equivalent;
  (b) $R_{11}$ and $R_{12}$ are each independently selected from methyl or methyl functional group equivalent;
  (c) $R_{13}$ and $R_{14}$ are each independently selected from the group consisting of amide, carboxylic acid, cyano, and cyano functional group equivalent.

In one embodiment, the compound of formula III is selected from the group consisting of: 2,3,7-tri(formylamino)-4,6-dimethyl-1,9-phenazinedicarbonitrile; 7-amino-2,3-di(formylamino)-4,6-dimethyl-1,9-phenazinedicarbonitrile; 3-amino-2,7-di(formylamino)-4,6-dimethyl-1,9-phenazinedicarbonitrile; 2-amino-3,7-di(formylamino)-4,6-dimethyl-1,9-phenazinedicarbonitrile; 2,3-diamino-7-(formylamino)-4,6-dimethyl-1,9-phenazinedicarbonitrile; 2,7-diamino-3-(formylamino)-4,6-dimethyl-1,9-phenazinedicarbonitrile; 3,7-diamino-2-(formylamino)-4,6-dimethyl-1,9-phenazinedicarbonitrile; and 2,3,7-triamino-4,6-dimethyl-1,9-phenazinedicarbonitrile.

Another aspect of the invention provides a composition, useful as an intermediate in the synthesis of 6-[(4,5-Dihydro-1H-imidazol-2-yl)amino-]-7-methyl-1H-benzimidazole-4-carbonitrile, comprising a compound of formula IV:

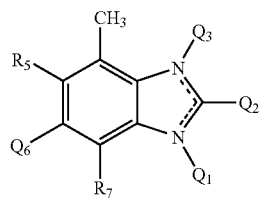

(IV)

wherein:
  (a) $Q_1$ is selected from the group consisting of hydrogen, hydrogen functional group equivalent, and nil;
  (b) $Q_2$ is selected from hydrogen or hydrogen functional group equivalent;
  (c) $Q_3$ is selected from the group consisting of hydrogen, hydrogen functional group equivalent, and nil;
  (d) $R_5$ is selected from the group consisting of hydrogen, nitro, (dichloromethylene)amino, and formylamine;
  (e) $Q_6$ is selected from hydrogen or hydrogen functional group equivalent; and
  (f) $R_7$ is selected from the group consisting of carboxylic acid, amide, and cyano;
  (g) provided that when $R_7$ is carboxylic acid, $R_5$ is not (dichloromethylene)amino;
  (h) provided that when $R_7$ is amide, $R_5$ is not (dichloromethylene)amino or hydrogen; and
  (i) provided that $Q_1$ or $Q_3$ is nil, but $Q_1$ and $Q_3$ are not both nil.
  (j) or tautomer thereof.

In one embodiment, the compound of formula IV is selected from the group consisting of: 7-Methyl-1H-benzimidazole-4-carboxylic acid; 7-Methyl-6-nitro-1H-benzimidazole-4-carboxylic acid; 6-(Formylamino)-7-methyl-1H-benzimidazole-4-carboxylic acid; 6-(Formylamino)-7-methyl-1H-benzimidazole-4-carbonitrile; 6-Amino-7-methyl-1H-benzimidazole-4-carboxylic acid; 6-Amino-7-methyl-1H-benzimidazole-4-carboxamide; 7-methyl-6-nitro-1H-benzimidazole-4-carboxamide; and 6-[(Dichloromethylene)amino]-7-methyl-1H-benzimidazole-4-carbonitrile. In another embodiment, the compound of formula IV is 6-Amino-7-methyl-1H-benzimidazole-4-carbonitrile substantially free of 2,3,7-triamino-4,6-dimethyl-1,9-phenazinedicarbonitrile.

Another aspect of the invention provides a composition, useful as an intermediate in the synthesis of 6-[(4,5-Dihydro-1H-imidazol-2-yl)amino-]-7-methyl-1H-benzimidazole-4-carbonitrile, comprising a compound of formula V:

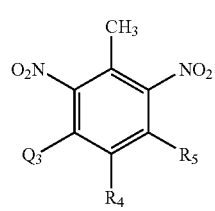

(V)

wherein:
  (a) $Q_3$ is selected from hydrogen or hydrogen functional group equivalent;
  (b) $R_4$ is selected from carboxylic acid or cyano;

(c) R$_5$ is selected from amino or nitrogen/one carbon equivalent conjugate; and (d) provided that when R$_5$ is amino, R$_4$ is not cyano.

In one embodiment, the compound of Formula (V) is N'-(6-Cyano-3-methyl-2,4-dinitrophenyl)-N,N-dimethyl-methanimidamide.

Another aspect of the invention provides a composition, useful as an intermediate in the synthesis of 6-[(4,5-Dihydro-1H-imidazol-2-yl)amino-]-7-methyl-1H-benzimidazole-4-carbonitrile, comprising a compound of formula (VI):

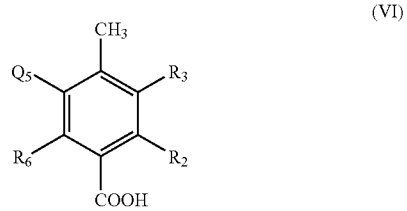

(VI)

wherein:
(a) R$_2$ is selected from hydrogen or nitro;
(b) R$_3$ is selected from formylamino or amino;
(c) Q$_5$ is selected from hydrogen, and hydrogen functional group equivalent;
(d) R$_6$ is selected from the group consisting of hydrogen, bromo, and hydrogen functional group equivalent; and
(e) provided that when R$_3$ is amino, R$_2$ is hydrogen and R$_6$ is bromo.

In one embodiment, the compound of Formula (VI) is selected from the group consisting of 3-(Formylamino)-4-methyl-benzoic acid; 3-(Formylamino)4-methyl-2-nitrobenzoic acid; 2-Bromo-5-(formylamino)4-methyl-benzoic acid; 5-Amino-2-bromo-4-methyl-benzoic acid; and 6-Bromo-3-(formylamino)-4-methyl-2-nitro-benzoic acid.

One aspect of the invention provides for a method of making intermediate 4-Methyl-3,5-dinitrobenzonitrile in a one step, one pot reaction comprising amidating and dehydrating 4-Methyl-3,5-dinitrobenzoic Acid by an amidating/dehydrating agent in a high boiling, polar aprotic solvent yielding said 4-Methyl-3,5-dinitrobenzonitrile, wherein the amidating/dehydrating agent is sulfamide and phosphorus oxychloride. In one embodiment, the high boiling, polar aprotic solvent is sulfolane.

One aspect of the invention provides for a method of making intermediate 2-Amino-4-methyl-3,5-dinitrobenzonitrile comprising aminating 4-Methyl-3,5-dinitrobenzonitrile with an aminating agent in a presence of a base in a polar aprotic solvent yielding said 2-Amino-4-methyl-3,5-dinitrobenzonitrile, wherein the base is lithium tert-butoxide and the aminating agent is 4-amino-1,2,4-triazole. In one embodiment, the polar aprotic solvent is selected from dimethyl sulfoxide or N,N-dimethylformamide.

One aspect of the invention provides for a method of making 6-[(4,5-Dihydro-1H-imidazol-2-yl)amino-]-7-methyl-1H-benzimidazole-4-carbonitrile that is substantially free of 2,3,7-triamino-4,6-dimethyl-1,9-phenazinedicarbonitrile.

One aspect of the invention provides for a method of making anhydrous monoacetate form of 6-[(4,5-Dihydro-1H-imidazol-2-yl amino-]-7-methyl-1H-benzimidazole-4-carbonitrile that is substantially free of 2,3,7-triamino-4,6-dimethyl-1,9-phenazinedicarbonitrile.

Lastly, one aspect of the invention provides for an anhydrous monoacetate form of 6-[(4,5-Dihydro-1H-imidazol-2-yl)amino-]-7-methyl-1H-benzimidazole-4-carbonitrile.

DETAILED DESCRIPTION OF THE INVENTION

I. Definitions and Usage of Terms:

The following is a list of definition for terms used herein:

The term "functional group equivalent," as used herein, is a functional group from which a particular functional group can be produced chemically. See Corey, E. J., & Xue-Min Cheng, *The Logic of Chemical Synthesis* (1989, published by John Wiley & Sons). Many suitable functional group equivalent transformations are described in Larock, Richard C., *Comprehensive Organic Transformations: A Guide to Functional Group Preparations*, second edition (1999, published by John Wiley & Sons). For example, an individual skilled in the art will recognize that the —CH$_2$Br functional group is a "methyl functional group equivalent", because the —CH$_3$ (methyl) group can be produced from the —CH$_2$Br group, by chemical reduction. In another example, the —CONH$_2$ group is a "cyano functional group equivalent", because the —CN (cyano) group can be produced from the —CONH$_2$ group by chemical dehydration. In another example, the —NO$_2$ group is an "amino functional group equivalent, because the —NH$_2$ (amino) group can be produced from the NO$_2$ group by chemical reduction. In another example, the —CHO group is a "carboxylic acid functional group equivalent", because the —CO$_2$H (carboxylic acid) group can be produced from the —CHO group by chemical oxidation. In yet another example, the —Br group is a "hydrogen functional group equivalent", because the —H (hydrogen) group can be produced from the —Br group by chemical reduction.

A subset of "functional group equivalents" is a functional group that is derivitized with a "protecting group" or "protective group". Often the skilled artisan utilizes protecting group moieties to accomplish increased yields or to avoid the undesired reactions. These reactions are found in the literature and are also well within the scope of the skilled artisan. Examples of many of these manipulations can be found, for example, in Green, Theodora. W., & Peter G. M. Wuts, editors, *"Protective Groups in Organic Synthesis"*, Third Edition (1999, published by John Wiley & Sons, Inc.). Clearly other terms employed herein are consistent with the term "protecting group." For example, a compound that has one or more protecting group moieties in place may be referred to as a "protected form" or as simply "protected" and is prepared using a "protection reaction" employing a "protecting agent" and that a subsequent step or steps may be employed to remove the protecting groups via "deprotection reactions" employing "deprotecting agents." Functional groups within the scope of this application that may be "protected" include carboxylic acids (Greene at pages 369-453), and amines (Greene at pages 494-653). As such, for example, an amine that is protected may be referred to as a "protected amine." The term "aromatic protecting group," as used herein, is a subset of a "protecting group moiety" that includes those protecting group moieties that may be introduced into aromatic ring systems. Such "aromatic protecting groups" may include halogens, such as bromine, —SO$_3$H, —NO$_2$, —COOH or -tertiary butyl, inter alia. Examples of halogenation reagents useful as aromatic protecting group and conditions thereof is described in Larock, Richard C., *Comprehensive Organic Transformations: A Guide to Func-* tional Group Preparations, second edition (1999, published by John Wiley & Sons). A preferred halogen is bromine. See Effenberger, Franz, "How Attractive is Bromine as a Protecting Group in Aromatic Chemistry?" by Franz Effenberger (Angewande Chemie, International Edition, 2002, Vol. 41, pg 1699-1670); Larock at pages 619-628. Non-limiting bromination reagents include N-bromosuccinimide, phosphorous tribromide and PBr$_3$. A preferred bromination agent is N-bromosuccinimide. Debromination reagents are described in Larock at pages 29-39.

The term "amidating agent," as used herein, refers to those chemical agents that are capable of converting a carboxylic acid functionality into a amide functionality. Non-limiting examples of suitable amidating agents are described in Larock at pages 1941-1949.

The term "nitrogen/one carbon equivalent conjugate," as used herein, refers to those functional groups wherein a nitrogen is linked to a carbon-based functional group, such that the carbon-based functional group, upon one or more chemical reactions, leads to the carbon that comprises the —N—C=N— system in a benzimidazole ring, and accordingly, the nitrogen leads to one of the nitrogens comprising the —N—C=N— system in a benzimidazole ring. While not intending to be limited by example, the —NH$_2$CHO and —N=C—N(CH$_3$)$_2$ functional groups would be examples of such nitrogen/one carbon equivalent conjugates as in compounds A and B, respectively, in Scheme A below. As used herein, a "nitrogen/one carbon equivalent conjugate" may be formed by reacting a suitable aromatic amine with a suitable "cyclization agent" (vide supra). For example, the —N=C—N(CH$_3$)$_2$ "nitrogen/one carbon equivalent conjugate" (as in compound B) may be formed by reacting a suitable aromatic amine with the "cyclization agent" N,N-dimethylformamide dimethyl acetal.

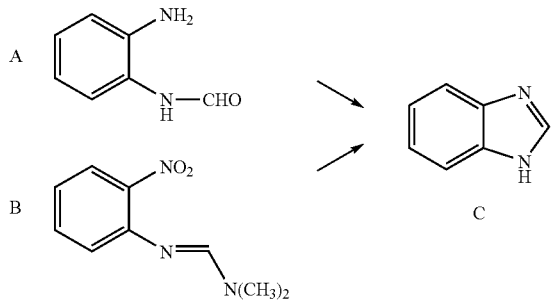

Scheme A

The term "amide dehydrating agent," as used herein, refers to those chemical agents that are capable of converting an amide functionality into a nitrile functionality. Non-limiting examples of suitable amide dehydrating agents are described in Larock at pages 1983-1985.

The term "amidating/dehydrating agent," as used herein, refers to those chemical agents that are capable of converting a carboxylic acid functionality into a nitrile functionality, in a single pot. Non-limiting examples of amidating/dehydrating agent are described in Larock at pages 1949-1950. Specific examples include: NH$_3$/silica gel; NH$_3$/ethyl polyphosphate; urea; sulfonamides, such as benzenesulfonamide or sulfamide; inter alia. Another reagent system includes employing sulfamide and thionyl chloride in sulfolane (A. Hulkenberg et al., Tetrahedron Letters, 1982, Vol. 23, 1505-1508), and it is recognized that this transformation may also proceed through an intermediate acid chloride.

The term "aminating agents," as used herein, refers to those chemical agents that are capable of adding an amino group to a molecule. Non-limiting examples of aminating agents are described in Larock at pages 388-438. Additionally, one skilled in the art would recognize that one could employ an aminating agent that adds an amine group through a "vicarious nucleophilic substitution" which is often referred to as simply "VNS." Non-limiting examples of aminating agents that react in a VNS fashion include sulfenamides, such as N,N-tetramethylenethiocarbamoyl sulfenamide, 2,4,6-trichlorobenzenesulfenamide, and 2-benzothiazolesulfenamide, in the presence of bases such as potassium tert-butoxide, potassium hydroxide in liquid ammonia, inter alia, as described by Makosa et al (Journal of Organic Chemistry, 1992, Vol. 57, pages 47844785). Another example of an aminating agent that reacts in a VNS fashion is 4-amino-1,2,4-triazole in the presence of potassium tert-butoxide, as described by Katritzky et al (Journal of Organic Chemistry, 1986, Vol. 51, pages 5040-5041). Yet another example of aminating agents that react in manner similar to a VNS include O-alkylhydroxylamines, such as O-ethylhydroxylamine, O-methylhydroxylamine, inter alia, in the presence of bases, such as potassium tert-butoxide, lithium tert-butoxide, inter alia, and a copper compound, such as CuBr, CuI, CuCl$_2$, Cu(acac)$_2$, Cu(OAc)$_2$, Cu(NO$_3$)$_2$, CuCl, inter alia, as described by Seko et al (Journal of The Chemical Society, Perkin Transactions 1, 1999, pages 1437-1444). Similarly, in the case of dinitroarenes, a suitable aminating agent is hydroxylamine in the presence of a base as described by Nasielski-Hinkenes, et al (Synthetic Communications, 1984, Vol. 19 page 511) and Meisenheimer at al (Chemishe Berichte, 1906, Vol. 39, page 2533).

The term "cyclization agent," as used herein, refers to those chemical agents that react with a substrate to allow a cyclization reaction to take place, in one or more synthetic steps. In the context of the present invention, a cyclization agent reacts to install a single carbon between two nitrogen functionalities to provide the imidazole portion of a benzimidazole ring system. Such single carbon sources or "one carbon equivalents" are well known in the art and include agents such as formic acid, dialkylformamide dialkyl acetals, such as N,N-dimethylformamide dimethyl acetal, N,N-dimethylformamide diethyl acetal, inter alia, trialkylorthoformates, such as triethylorthoformate, trimethylorthofomate, inter alia, EMM reagents, such as ethoxymethylenemalononitrile, inter alia, Vilsmier reagents, such as chloro-N,N-dimethylformiminium chloride, inter alia. Some synthetic approaches for benzimidazoles are provided in the text Grinmmin, Imidazole and Benzimidazole Synthesis (1997, Academic Press).

The term "deformylating agent," as used herein, refers to those chemical agents that are capable of removing the formyl group from a formamide derivative to provide an amine group (e.g., conversion of a HCONH— group to an NH$_2$ group). An individual skilled in the art will recognize that formamides are commonly used as protecting groups for amine functionalities, and may be installed intentionally for further conversions to other functionalities, or be formed as byproducts. An individual skilled in the art would also recognize that formamide derivatives could be cleaved under a variety of acid and basic conditions. Non-limiting examples of deformylating agents are described in Greene at page 551-552. Specific examples include: HCl, water in dioxane; hydrazine in ethanol; hydrogen and palladium on carbon; HCl in tetrahydrofuran; sodium hydroxide in water; inter alia.

The term "formylating agent," as used herein, refers to those chemical agents that are capable of converting an amine to a formamide derivative (e.g., conversion of a $NH_2$— group to an HCONH— group). An individual skilled in the art will recognize that formamides are commonly used protecting groups for amine functionalities, and may be installed intentionally for further conversions to other functionalities, or be formed as byproducts. Non-limiting examples of formylating agents are described in Greene at page 551. Specific examples of formylating agents include: 98% $HCO_2H$ and $Ac_2O$, $HCO_2H$ and DCC in pyridine, $HCO_2Et$, formic acid and triethylorthoformate, inter alia.

The term "hydrogen donor," as used herein, refer to those chemical agents that are capable of donating hydrogen in a "catalytic transfer hydrogenation reaction." See Brieger and Nestrick, Chemical Reviews, (1974), Vol. 74, No. 5, pages 567-580 and Johnstone et al., Chemical Reviews, (1985), Vol. 85, No. 2, pages 129-170. Non-limiting examples of hydrogen donors include: cyclohexene, various alcohols, such as ethanol and 1,2-ethanediol, and certain acids, such as ascorbic acid and formic acid.

The term "nitro group reducing agent," as used herein, refers to those chemical agents that are capable of converting a nitro group (—$NO_2$) to an amine group (—$NH_2$). Non-limiting examples of nitro group reducing agents are described in Larock at pages 821-828. Specific examples include: $H_2$/Raney nickel, $H_2$/palladium on carbon, $H_2$/platinum hydroxide on carbon, inter alia. See also Hudlicky, *Reductions in Organic Chemistry* (Ellis Harwood Limited, 1984). It is also recognized that transfer hydrogenation systems can be used as nitro group reducing agents, as described by Johnstone et al (Chemical Reviews, 1985, Vol. 85, pages 129-170). Such transfer hydrogenation conditions include palladium on carbon/cyclohexene, palladium on carbon/formic acid, palladium on carbon/triethylammonium formate, inter alia. In particular, certain "non-ferrous metal hydrogenation catalysts" (vide infra) are particularly useful for the subclass of "nitro group reducing agents" known as "catalytic hydrogenation" which is well known in the art and described in such texts as Rylander, *Hydrogenation Methods* (Academic Press, 1985), and in the review by Johnstone.

The term "non ferrous metal hydrogenation catalysts," as used herein, refers to those agents that are capable of reducing compounds in the presence of hydrogen, either in a gaseous form or from a hydrogen donor, as described, for example, by Johnstone. Non-limiting examples of non ferrous metal hydrogenation catalysts are described in Hudlicky at pages 1-13. Specific examples include: platinum, palladium, rhodium, ruthenium, and nickel. It is also recognized that these metals are often precipitated on materials having large surface area such as activated charcoal (carbon), silica gel, alumina, calcium carbonate, barium sulfate, inter alia. These materials are often referred to in the art as "supported catalysts." See Hudlicky at pg. 6. Preferred supported catalysts are palladium on carbon, and platinum on carbon. It is also recognized that the reactivity of some metal hydrogenation catalysts may be modified by the presence of sulfur (sulfided catalysts), quinoline, lead acetate, inter alia. See Hudlicky at page 5-9. A preferred modified non ferrous hydrogenation catalyst is sulfided platinum on carbon. Non ferrous metal hydrogenation catalysts are commercial available, inter alia, from Engelhard Corporation, (Carteret, N.J., USA and Rome, Italy), and are preferably selected from the group consisting of C5002, CP126, CP94, CP110, CP41, C3759, 43045 and CP100. Similar catalysts are also available from Degussa (Parsippany, N.J., USA and Frankfurt, Germany).

The term "nitrating agents," as used herein, refers to those chemical agents that are capable of adding a nitro group to a molecule. Non-limiting examples of nitrating agents are described by March at pages 522-525. Specific examples of nitrating agents include nitric acid alone, a mixture of nitric and sulfuric acids, $N_2O_5$ in $CCl_4$ in the presence of $P_2O_5$, a mixture of $NaNO_2$ and trifluoroacetic acid, and nitronium salts, such as $NO_2BF_4$, inter alia, or clay supported cupric nitrate, inter alia.

The term "polar aprotic solvents," as used herein, are well known in the art, are often referred to as "dipolar aprotic solvents," and are generally characterized as having large dielectric constants, sizeable dipole moments, and typically do not act as hydrogen bond donors. See March at page 358. Non-limiting examples of polar aprotic solvents include N,N-dimethylformamide (DMF), dimethylsulfoxide, acetonitrile, acetone, sulfur dioxide, hexamethylphosphoramide (HMPA), benzonitrile, N,N-dimethylacetamide, dimethylsulfone, 1-methyl-2-pyrrolidinone, nitrobenzene, nitromethane, sulfolane, 1,1,3,3-tetramethylurea, and dimethyl propylene urea. See also Reichardt, Christian, *Solvents and Solvent Effects in Organic Chemistry*, Second Edition (Published by VCH, 1990) at page 69.

The term "tautomer", as used herein, is well known in the art. The present invention includes tautomers of the indicated structures. For example, when tautomer D of a molecule is shown (see Scheme A), it is understood to include tautomer E. In another example, when tautomer F is shown, it is understood to include tautomer G. Thus, the disclosure of one tautomeric form discloses each and all of the tautomers.

Scheme B

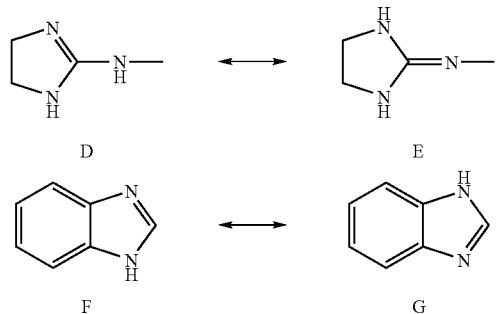

The skilled artisan will understand the definitions and usage of other terms herein, consistent with a reference text, such as: Morris, Christopher editor, *Academic Press Dictionary of Science and Technology* (1992, published by Academic Press, Inc.); and the texts by: March; Corey and Cheng; Carey and Sundberg; Fieser & Feiser; Paquette; and Trost and Fleming (vide infra).

II.  6-[(4,5-Dihydro-1H-imidazol-2-yl)amino-]-7-methyl-1H-benzimidazole-4-carbonitrile The present invention is based, in part, on the surprising discovery of a novel mutagenic phenazine produced during process scale-up of 6-[(4,5-Dihydro-1H-imidazol-2-yl)amino-]-7-methyl-1H-benzimidazole-4-carbonitrile (1):

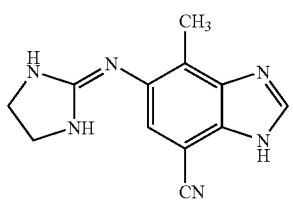

using previously disclosed methods. The phenazine, specifically 2,3,7-triamino-4,6-dimethyl-1,9-phenazinedicarbonitrile (2):

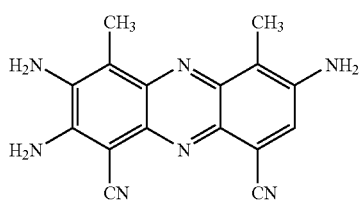

is produced in pharmaceutically unacceptable levels using these previous methods. Based on dose/response studies using an Ames Test, the mutagenic impurity (2) is shown to elicit a positive response when present at level about 1 ppm (parts per million) in 6-[(4,5-Dihydro-1H-imidazol-2-yl)amino-]-7-methyl-1H-benzimidazole-4-carbonitrile (1) and its various salt forms. Low levels of this phenazine impurity can be detected by those methods well known in the art such as HPLC with fluorescence detection. Suitable examples of such assays are described in Examples 1, 2, and 3 herein. A suitable preparation of labeled $^{15}N_4$-2,3,7-Triamino-4,6-dimethyl-1,9-phenazinedicarbonitrile is described in Example 4 herein. A suitable preparation of non-labeled 2,3,7-Triamino-4,6-dimethyl-1,9-phenazinedicarbonitrile is described in Example 19 herein.

III. Methods of Making Intermediate of Formula (II)

Without wishing to be bound by theory, it is the nitro reduction and cyclization steps, according to previous methods, from certain aromatic intermediates to yield the fused ring benzimidazole nucleus, that produces a phenazine impurity of formula (III):

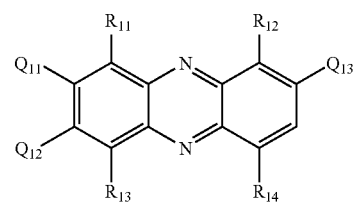

wherein $Q_{11}$, $Q_{12}$, $Q_{13}$, $R_{11}$, $R_{12}$, $R_{13}$, and $R_{14}$ are as previously defined. More specifically exemplified in the Scheme C below, it is the use or formation of significant levels of certain ortho-diamine intermediates (H) that produces the phenazine impurity (Route B); nonetheless, such intermediates are often used in the synthesis of benzimidazoles (Route A). The use of such intermediates to form phenazines is known in the art (see page 11 of Chapter 1, "General Methods for Synthesis of Phenazines" in the monograph on Phenazines, as part of the series "The Chemistry of Heterocyclic Compounds", Interscience Publishers Inc. New York, 1957). It is proposed in the art that such ortho-diamines (H) may lead to the formation of so-called "benzoquinone di-imine" intermediates (K and N), which in turn lead to phenazine compounds (O) and (P) (for example, see Corbett et al., J. Chem. Soc., Perkin Trans. II, 1975, pages 728-734). It is also recognized that various hydroxylamine compounds, such as (O), may also be involved in phenazine formation.

Scheme C

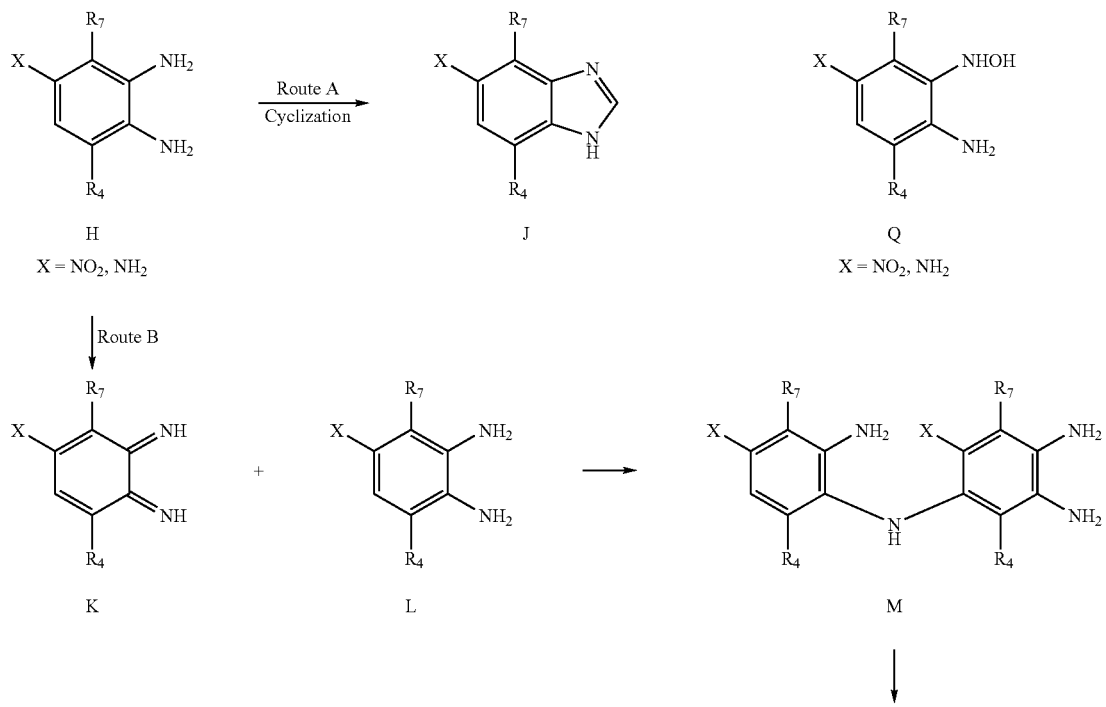

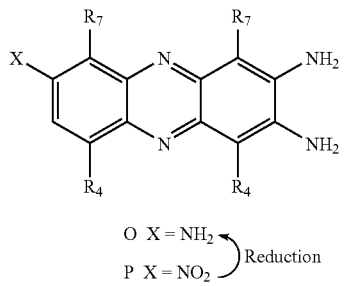

O X = NH₂
P X = NO₂  } Reduction

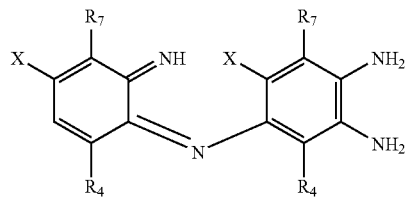

N

The present invention minimizes the synthesis of a phenazine of formula (III) by providing for a method of making a preferred intermediate in the synthesis of 6-[(4,5-Dihydro-1H-imidazol-2-yl)amino-]-7-methyl-1H-benzimidazole-4-carbonitrile of formula (II):

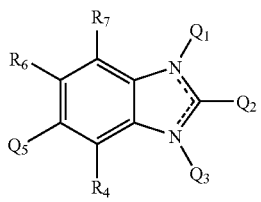

wherein: $Q_1$, $Q_2$, $Q_3$, $R_4$, $Q_5$, $R_6$, and $R_7$ are previously defined;

comprising:

a) providing a compound of formula (I):

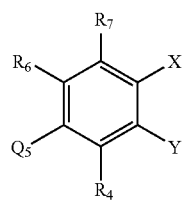

wherein: X, Y, $R_4$, $Q_5$, $R_6$, and $R_7$ are previously defined;

b) cyclizing the formula (I) compound in a single pot by using a non ferrous metal hydrogenation catalyst in the presence of hydrogen or a hydrogen donor, and optionally a cyclization agent, to yield the compound of formula (II). A cyclization agent may be optionally used when X or Y in formula (I) is not a nitrogen/one carbon equivalent conjugate.

Without wishing to be bound by theory, one embodiment the present invention significantly reduces the formation of the aforementioned quinone di-imine type intermediates (see Scheme C), by performing the reduction and cyclization steps in a single pot in a medium that induces cyclization to the benzimidazole ring system over the formation of the phenazine type ring system, by performing the reduction in a formic acid which serves as both a hydrogen source and a cyclization agent, essentially trapping the reduced intermediate with a one carbon equivalent and inducing cyclization, thus avoiding the formation of significant amounts of ortho-diamine intermediates (H). In another embodiment, without wishing to be bound by theory, the present invention significantly reduces or eliminates the formation of the phenazine ring system by blocking the potentially reactive amine group as a nitrogen/one carbon equivalent conjugate which then forms the desired benzimidazole system upon reduction of the ortho amino group and the subsequent facile condensation.

Many compounds of a formula (II) are contemplated within the scope of present invention. In one embodiment, the compound of formula (II) is selected from the group consisting of: 6-(Formylamino)-7-methyl-1H-benzimidazole-4-carboxylic acid; 6-Amino-7-methyl-1H-benzimidazole-4-carbonitrile; 6-(Formylamino)-7-methyl-1H-benzimidazole-4-carbonitrile; 6-(Formylamino)-7-methyl-1H-benzimidazole-4-carboxamide; and 7-Methyl-1H-benzimidazole-4-carboxylic acid. In one embodiment, the method provides the synthesis of a formula (II) compound substantially free of a compound of formula (III). As used herein, "substantially free" means an amount of formula (III) that is pharmaceutically acceptable. In another embodiment, the method provides the synthesis of a formula (II) compound comprising less than about 2 parts per million of formula (III) compound. In another embodiment, the compound of formula (II) is 6-Amino-7-methyl-1H-benzimidazole-4-carbonitrile and is substantially free, preferably less than about 2 parts per million (ppm), more preferably less than about 1 ppm, of the formula (III) compound 2,3,7-triamino-4,6-dimethyl-1,9-phenazinedicarbonitrile. Similarly, many suitable intermediate compounds of formula (I) are also contemplated within the scope of the present invention. In one embodiment, the compound of formula (I) is selected from the group consisting of: N'-(6-Cyano-3-methyl-2,4-dinitro-phenyl)-N,N-dimethyl-methanimidamide; 2-Amino-4-methyl-3,5-dinitro-benzonitrile; 2-Amino-4-methyl-3,5-dinitro-benzamide; 6-Bromo-3-(formylamino)₄-methyl-2-nitro-benzoic acid; 3-Amino-4-methyl-2-nitro-benzoic acid; and 3-(Formylamino)-4-methyl-2-nitro-benzoic acid.

A. Preparation of Formula I Intermediates

Formula I intermediates of the invention can be prepared using a variety of procedures. Particularly preferred, although not intended to be limiting, syntheses are described in the following general reaction schemes. Starting compounds are known, commercially available, or made by known methods. For example, in General Scheme I, starting compound 4-Methyl-3,5-dinitrobenzoic Acid (3) is converted to intermediate 4-Methyl-3,5-dinitrobenzonitrile (4) in a one step one pot reaction comprising amidating and dehydrating the starting compound (3) by an amidating/dehydrating agent in a high boiling, polar aprotic solvent to yield intermediate (4). In one embodiment, the amidating/dehydrating agent is a mixture of sulfamide and phosphorus oxychloride and the high boiling, polar aprotic solvent is sulfolane. In a preferred embodiment, 1 equivalent of 4-Methyl-3,5-dinitrobenzoic Acid and about 1.3 to about 3.3 equivalents, preferably about 2.3 equivalents of sulfamide are stirred in sulfolane at a temperature of about 25° C. to about 120° C., and about 1.4 to about 2.0 equivalents of phosphorus oxychloride are added over about 30 to about 120 minutes, and then the reaction mixture is stirred at a temperature of about 120° C. to about 130° C., until the reaction is complete. See Example 5. Alternatively, the preparation of intermediate (4) may also be accomplished in two steps by amidating starting compound (3) using an amidating agent to intermediate 4-Methyl-3,5-dinitrobenzamide (6) and then dehydrating intermediate (6) using a amide dehydrating agent to intermediate (4). See Examples 6, 7, and 8 herein, respectively.

Formula (I) intermediate 2-Amino-4-methyl-3,5-dinitrobenzonitrile (5) is prepared by aminating intermediate (4) with an aminating agent in the presence of a base in a polar aprotic solvent. In one embodiment, the aminating agent is 4-amino-1,2,4-triazole. In one embodiment, the base is selected from the group consisting of sodium methoxide, sodium hydride, potassium tert-butoxide, and lithium tert-butoxide. In one embodiment, the polar aprotic solvent is either N,N-dimethylformamide or dimethylsulfoxide. In a preferred embodiment, the base is lithium tert-butoxide. In a preferred embodiment, a solution of one equivalent of intermediate (4) and about 4 equivalents of 4-amino-1,2,4-triazole in dimethylsulfoxide is dosed into a mixture of about 3 equivalents of lithium tert-butoxide in dimethylsulfoxide, at a rate to maintain the reaction temperature below about 25° C., whereupon the reaction mixture is maintained at about 25° C. until the reaction is complete. See Example 5.

Intermediate (5) may also be prepared in an alternative order by aminating intermediate (6) by an aminating agent to Formula (I) intermediate 2-Amino-4-methyl-3,5-dinitrobenzamide (7) and then dehydrating intermediate (7) by an amide dehydrating agent to yield intermediate (5). See Example 9.

Intermediates such an intermediate (5) can be further derived to a nitrogen/one carbon equivalent conjugate such as Formula (I) intermediate N'-(6-Cyano-3-methyl-2,4-dinitro-phenyl)-N,N-dimethyl-methanimidamide (8). See Example 11.

In another example, per General Scheme 2, starting compound 3-Amino-4-methyl-benzoic acid (13) is converted to intermediate 3-(Acetylamino)4-methyl-benzoic acid (14) by the addition of an amino functional group equivalent or protecting group, such as an acetyl group, to yield intermediate (14). See Example 12. Alternatively, intermediate 3-(Formylamino)4-methyl-benzoic acid (17) is prepared by formylating starting compound (13) with a formylating agent wherein the formyl group acts as a protecting group moiety as well as a source of carbon in the cyclization step. One skilled in the art will readily appreciate that other protecting group moieties may be used. Intermediates (14) and (17) are nitrated by a nitrating agent to yield Formula (I) intermediate 3-(Acetylamino)-4-methyl-2-nitro-benzoic acid (15) and intermediate 3-(Formylamino)-4-methyl-2-nitro-benzoic acid (18), respectively. See Examples 12 and 13, respectively. Intermediate (15) is deprotected by a deprotecting agent to yield Formula (I) intermediate 3-Amino-4-methyl-2-nitro-benzoic acid (16).

In a preferred method, an aromatic protecting group is added to starting compound (13). For example, compound (13) is brominated by a brominating agent to yield intermediate 5-Amino-2-bromo-4-methyl-benzoic acid (19). Thereafter, intermediate (19) may be formylated by a formylating agent to yield intermediate 2-Bromo-5-(formylamino)-4-methyl-benzoic acid (20). Lastly, to yield Formula (I) intermediate 6-Bromo-3-(formylamino)4-methyl-2-nitro-benzoic acid (21), intermediate (20) is nitrated by a nitrating agent. See Example 14.

B. Intermediate Formula (I) Cyclization to Intermediate Formula (II)

A Formula (I) intermediate is cyclized in a single pot to a Formula (II) intermediate by using a non ferrous metal hydrogenation catalyst in the presence of a hydrogen or hydrogen donor and a cyclization agent to yield the compound of formula (II). A preferred non ferrous metal hydrogenation catalyst is sulfided platinum on carbon. In a preferred embodiment, the hydrogen donor and cyclization agent are one in the same and is formic acid. In one embodiment, the cyclization step is performed with formic acid and a non ferrous hydrogenation catalyst at a temperature of about 80-105° C. for about 1-9 hours. In a preferred embodiment, 2-Amino-4-methyl-3,5-dinitrobenzonitrile is cyclized to 6-(Formylamino)-7-methyl-1H-benzimidazole-4-carbonitrile in a one step, one pot reaction by using about 5-25% (dry basis, as a weight percentage of the substrate, 2-Amino-4-methyl-3,5-dinitrobenzonitrile) of sulfided platinum on carbon in the presence of about 50-60 molar equivalents of aqueous formic acid for about 1-3 hours at about 90-100° C. In a preferred embodiment, an intermediate of Formula (II) is produced that is substantially free of the Formula (III) phenazine.

Turning to General Scheme (1), intermediates (5) and (7) are cyclized in a single pot by using a non-ferrous metal hydrogenation catalyst in the presence of hydrogen or a hydrogen donor, to yield intermediates 6-(Formylamino)-7-methyl-1H-benzimidazole-4-carbonitrile (9), and 6-(Formylamino)-7-methyl-1H-benzimidazole-4-carboxamide (11), respectively. See Examples 5, 10 and 15. Alternatively, intermediate (5) is cyclized in a two step reaction sequence by first using a cyclization agent (to install a nitrogen/one carbon equivalent conjugate) to yield intermediate N'-(6-Cyano-3-methyl-2,4-dinitro-phenyl)-N,N-dimethyl-methanimidamide (8); and then secondly, by using a non-ferrous metal hydrogenation catalyst in the presence of hydrogen or a hydrogen donor to yield intermediate 6-Amino-7-methyl-1H-benzimidazole-4-carbonitrile (10). See Example 11.

Turning to General Scheme (2), intermediates (16), (18), and (21) are cyclized in a single pot by using a non-ferrous metal hydrogenation catalyst in the presence of hydrogen or a hydrogen donor to yield intermediate 7-Methyl-1H-benzimidazole-4-carboxylic acid (22). One skilled in the art will readily appreciate that the cyclization of intermediate (21) to intermediate (22) should be carried out under basic condition to effectively debrominate the Formula (II) intermediate. See Examples 12, 13, and 14, respectively.

IV. Methods of Making Intermediate 6-Amino-7-methyl-1H-benzimidazole-4-carbonitrile Without limitation, intermediate 6-Amino-7-methyl-1H-benzimidazole-4-carbonitrile (10) is a preferred intermediate in coupling the 4,5-Dihydro-2-(methylthio)-1H-imidazole-1-carboxylic Acid Methyl Ester "side chain" (29) thereto. Referring to General Scheme 1, intermediate (9) is deformylated by a deformylating agent to yield intermediate (10). Lastly, intermediate (11) is deformylated by a deformylating agent to yield intermediate 6-Amino-7-methyl-1H-benzimidazole-4-carboxamide (12), and thereafter is amide dehydrated by an amide dehydrating agent to yield intermediate (10). See Example 15. The assay described in Example 2 may then be used to analyze intermediate (10) for the level of 2,3,7-triamino-4,6-dimethyl-1,9-phenazinedicarbonitrile that is present. In a preferred embodiment, less than 2 parts per million of 2,3,7-triamino-4,6-dimethyl-1,9-phenazinedicarbonitrile is produced as a side product in yielding intermediate (10).

As to General Reaction Scheme 3, intermediate (22) (produced via, inter alia, General Scheme 2) is nitrated by a nitrating agent to yield intermediate 7-Methyl-6-nitro-1H-benzimidazole-4-carboxylic acid (23). In turn, intermediate (23) may either be amidated/dehydrated by an amidating/dehydrating agent to yield intermediate 7-Methyl-6-nitro-1H-benzimidazole-4-carbonitrile (24), or amidated by an amidating agent to yield intermediate 7-Methyl-6-nitro-1H-benzimidazole-4-carboxamide (25). Intermediate (24) is reduced by a nitro group reducing agent to yield intermediate (10). In turn, intermediate (25) is reduced by a nitro group reducing agent to yield intermediate 6-Amino-7-methyl-1H-benzimidazole-4-carboxamide, hydrochloric acid salt (26), and thereafter dehydrated by an amide dehydrating agent to yield intermediate (10). See Examples 13 and 14.

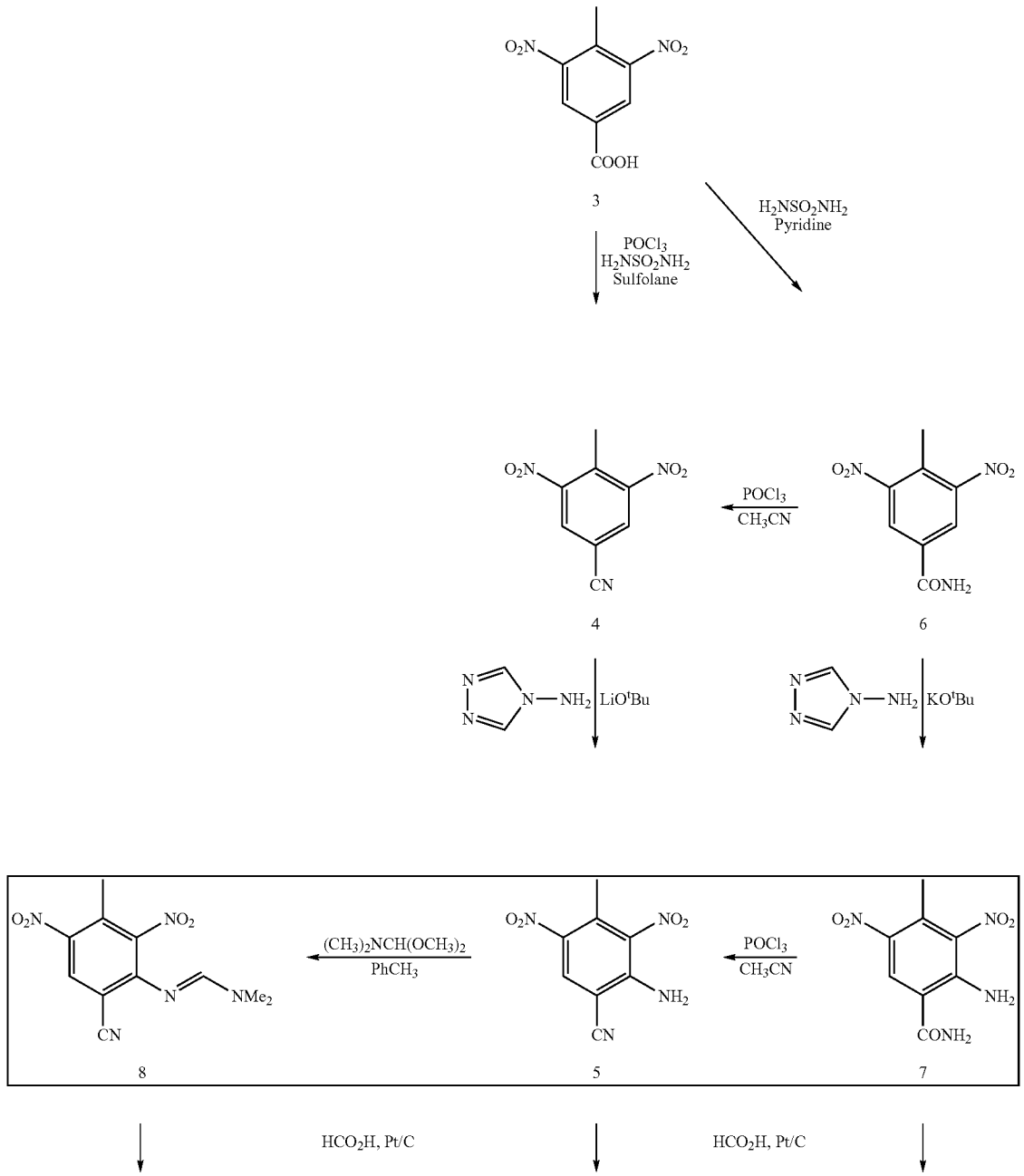

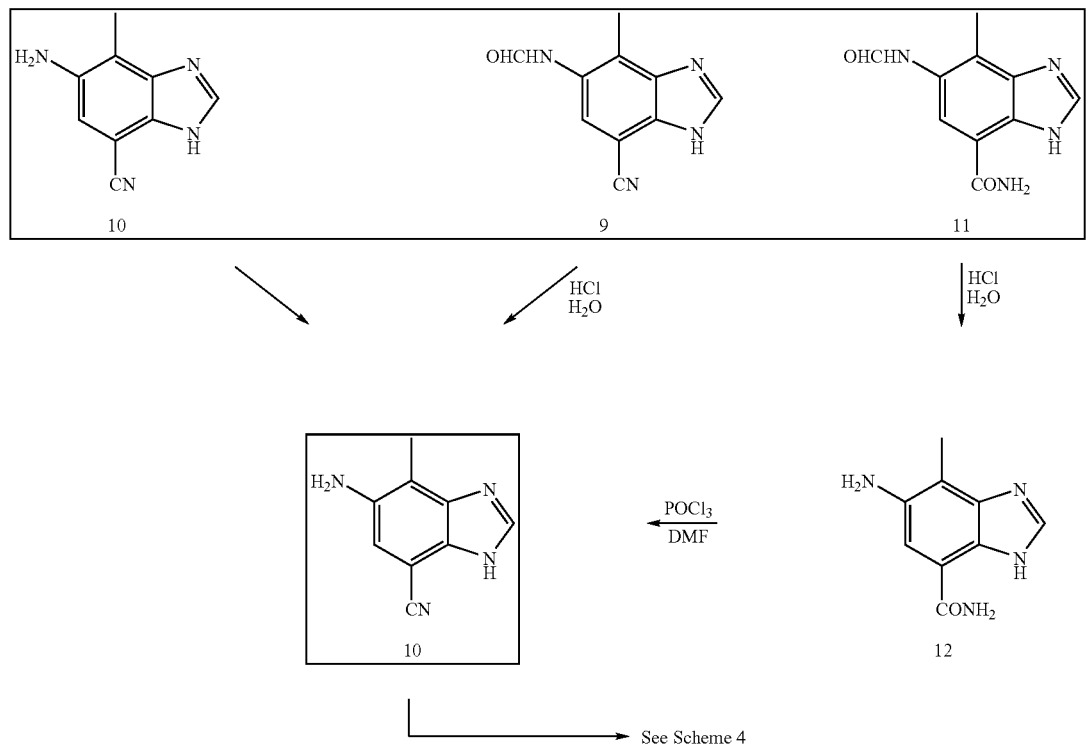
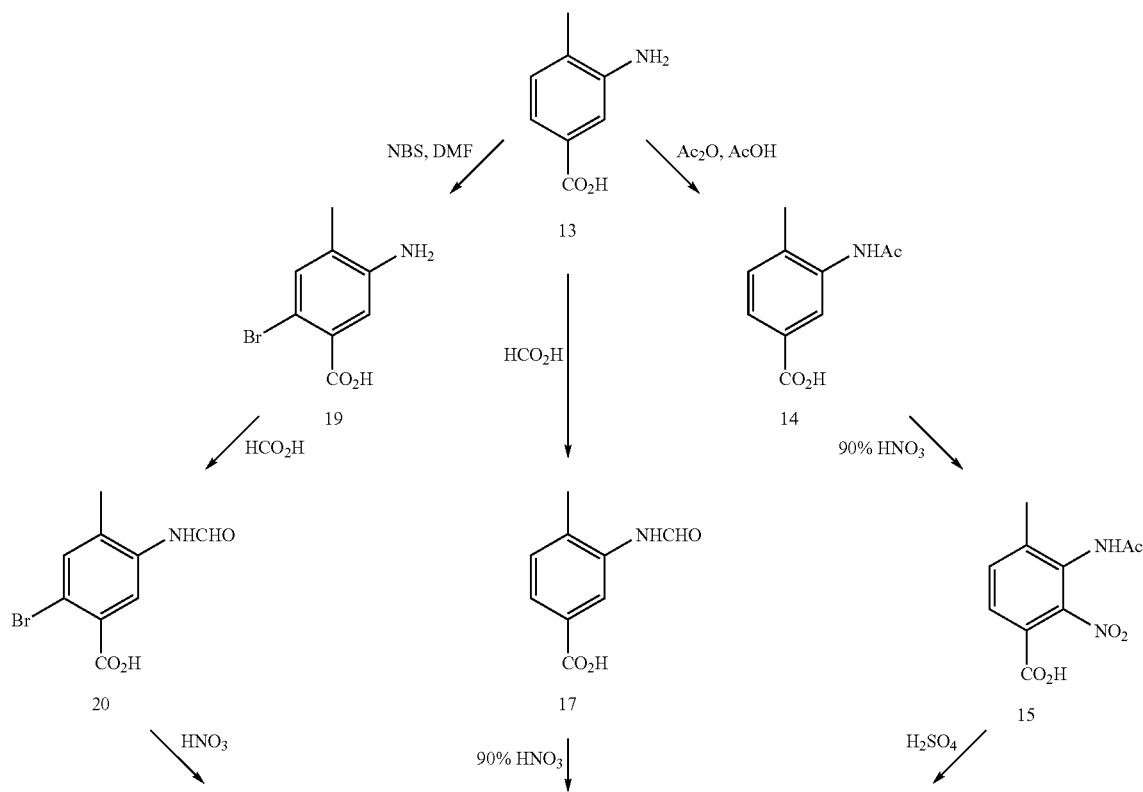
General Scheme 2

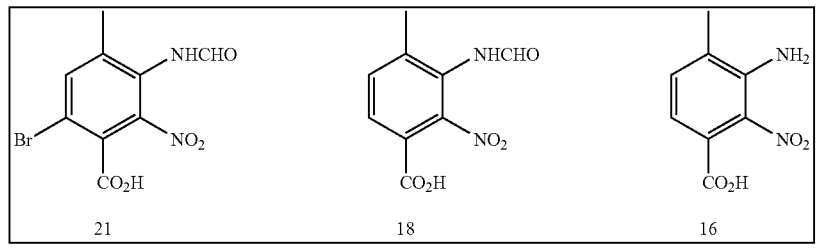
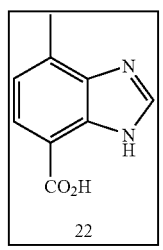
→ See Scheme 3
General Scheme 3
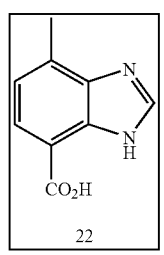
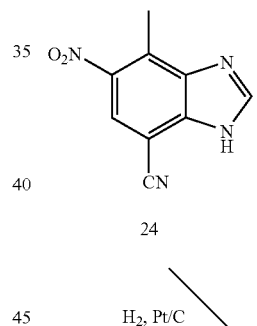
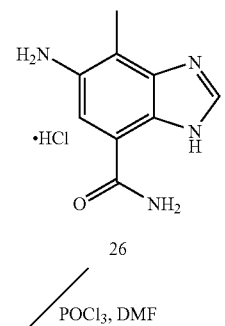
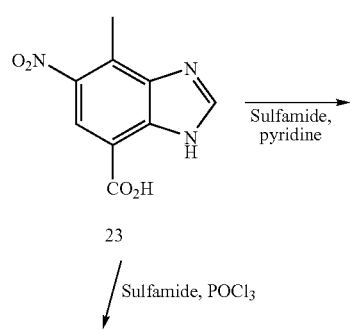
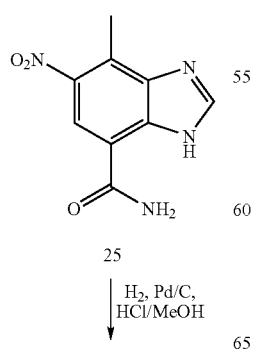
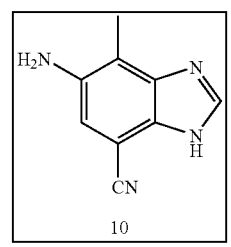
→ See General Scheme 4

V. Coupling intermediate 6-Amino-7-methyl-1H-benzimidazole-4-carbonitrile with side chain 4,5-Dihydro-2-(methylthio)-1H-imidazole-1-carboxylic Acid, Methyl Ester There are many suitable methods for coupling intermediate (10) with side chain 4,5-Dihydro-2-(methylthio)-1H-imidazole-1-carboxylic Acid, Methyl Ester (29). Referring to General Scheme (4), intermediate (10) is coupled to side chain (29) to yield intermediate 2-(7-Cyano-4-methyl-1H-benzimidazol-5-yl-imino)-imidazolidine-1-carboxylic Acid Methyl Ester (30), and thereafter deprotected to yield product 6-[(4,5-Dihydro-1H-imidazol-2-yl)amino-]-7-methyl-1H-benzimidazole-4-carbonitrile (31a) as the preferred anhydrous, monoacetate salt (which can be further purified by recrystallization to yield final product (31b)). See Example 5. The assay described in Example 3 may be used to analyze products (31a) and (31b) for the level of 2,3,7-triamino-4,6-dimethyl-1,9-phenazinedicarbonitrile that is present. In one embodiment, the preferred anhydrous monoacetate salt of 6-[(4,5-Dihydro-1H-imidazol-2-yl)amino-]-7-methyl-1H-benzimidazole-4-carbonitrile (31a) and (31b) that is produced is substantially free of 2,3,7-triamino-4,6-dimethyl-1,9-phenazinedicarbonitrile. In one embodiment, the preferred anhydrous monoacetate salt of 6-[(4,5-Dihydro-1H-imidazol-2-yl)amino-]-7-methyl-1H-benzimidazole-4-carbonitrile (31a) and (31b) that is produced contains less than 70 ppb (parts per billion), preferably less than 15 ppb, more preferably less than 5 ppb, of 2,3,7-triamino-4,6-dimethyl-1,9-phenazinedicarbonitrile. Other solvent systems that may be used to recrystallize product (31a) to yield final product (31b) include: ethanol/water, acetone/water, acetonitrile/water, tetrahydrofuran/water, methanol, N,N-dimethylacetamide, and acetonitrile. Although in General Scheme 4 intermediate (30) is carried forward without isolation, it may be isolated as shown in Example 16. Another method to attach the side chain includes Example 17. Still another suitable method is described in U.S. Pat. No. 6,066,740.

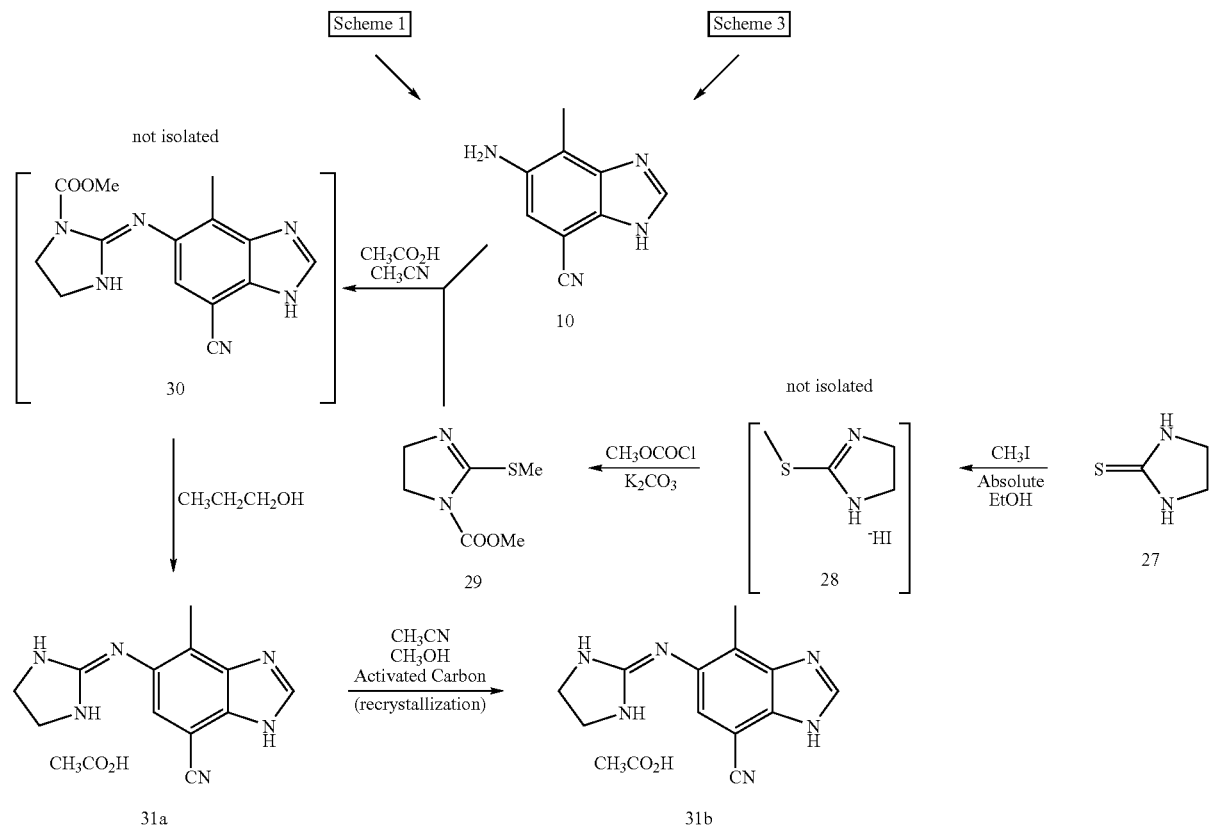

A comparison of the solubility of the presently claimed anhydrous monoacetate salt of 6-[(4,5-Dihydro-1H-imidazol-2-yl)amino-]-7-methyl-1H-benzimidazole-4-carbonitrile and that of previously disclosed sulfuric acid salt and free base form is presented as Example 18.

Lastly, it is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations, acylations, aromatic substitutions, both electrophilic and nucleophilic, etherifications, esterification and saponification and the like. Examples of these manipulations are discussed in standard texts, such as: "Advanced Organic Chemistry: Reactions, Mechanisms and Structure", fourth edition (1992, published by John Wiley & Sons) authored by Jerry March; "The Logic of Chemical Synthesis" (1989, published by John Wiley & Sons) authored by E. J. Corey and Xue-Min Cheng; Carey and Sundberg, "Advanced Organic Chemistry" (2 Volumes);

Fieser & Fieser, "Reagents for Organic Synthesis" (16 volumes); L. Paquette, "Encyclopedia of Reagents for Organic Synthesis" (8 volumes); Trost & Fleming, "Comprehensive Organic Synthesis" (9 volumes); and the like.

VI. Methods

6-[(4,5-Dihydro-1H-imidazol-2-yl)amino-]-7-methyl-1H-benzimidazole-4-carbonitrile substantially free of 2,3,7-triamino-4,6-dimethyl-1,9-phenazinedicarbonitrile, and the anhydrous monoacetate salt thereof, are useful for the treatment of a variety of diseases, disorders, and conditions that are modulated by alpha-2 adrenoceptors or by alpha-2 adrenoceptor activity. As used herein, the terms "disease," "disorder" and "condition" are used interchangeably. As used herein, a disorder described by the terms "modulated by alpha-2 adrenoceptors," or "modulated by alpha-2 adrenoceptor activity" refers to a disorder, condition or disease where alpha-2 adrenoceptor activity is an effective means of alleviating the disorder or one or more of the biological manifestations of the disease or disorder; or interferes with one or more points in the biological cascade either leading to the disorder or responsible for the underlying disorder; or alleviates one or more symptoms of the disorder. Thus, disorders subject to "modulation" include those for which: (1) The lack of alpha-2 activity is a "cause" of the disorder or one or more of the biological manifestations, whether the activity was altered genetically, by infection, by irritation, by internal stimulus or by some other cause; (2) The disease or disorder or the observable manifestation or manifestations of the disease or disorder are alleviated by alpha-2 activity. The lack of alpha-2 activity need not be causally related to the disease or disorder or the observable manifestations thereof; and (3) Alpha-2 activity interferes with part of the biochemical or cellular cascade that results in or relates to the disease or disorder. In this respect, the alpha-2 activity alters the cascade, and thus controls the disease, condition or disorder.

There are many such alpha-2 mediated disorders known in the art. See, e.g., WO 99/26942.

VII. Compositions

Another aspect of this invention provides for pharmaceutical compositions which comprise a safe and effective amount of 6-[(4,5-Dihydro-1H-imidazol-2-yl)amino-]-7-methyl-1H -benzimidazole-4-carbonitrile, substantially free of 2,3,7-triamino-4,6-dimethyl-1,9-phenazinedicarbonitrile, and the anhydrous monoacetate salt thereof. As used herein, "safe and effective amount" means an amount of a compound of the invention sufficient to significantly induce a positive modification in the condition to be treated, but low enough to avoid serious side effects (at a reasonable benefit/risk ratio), within the scope of sound medical judgment. A safe and effective amount of the compound of the invention will vary with the age and physical condition of the patient being treated, the severity of the condition, the duration of the treatment, the nature of concurrent therapy, the particular pharmaceutically-acceptable carrier utilized, and like factors within the knowledge of and expertise of the attending physician.

In addition to the compound of the invention, the compositions of this invention contain a pharmaceutically-acceptable carrier. The term "pharmaceutically-acceptable carrier," as used herein, means one or more compatible solid or liquid filler diluents or encapsulating substances which are suitable for administration to a human or lower animal. The term "compatible", as used herein, means that the components of the composition are capable of being commingled with the compound of the invention, and with each other, in a manner such that there is no interaction which would substantially reduce the pharmaceutical efficacy of the composition under ordinary use situations. Techniques for formulating pharmaceutical compositions are described in *Modern Pharmaceutics*, Vol. 7, (Banker & Rhodes, editors, 1979); Lieberman et al., *Pharmaceutical Dosage Forms: Tablets* (1981); and Ansel, *Introduction to Pharmaceutical Dosage Forms*, last edition.

VIII. EXAMPLES

Example 1

For the detection of 2,3,7-triamino-4,6-dimethyl-1,9-phenazinedicarbonitrile, at levels of about 0.05% and higher, in 6-[(4,5-Dihydro-1H-imidazol-2-yl)amino-]-7-methyl-1H-benzimidazole-4-carbonitrile and its various salt forms, and its precursors, one skilled in the art might employ reverse phase HPLC methodology with UV (ultraviolet) detection.

An example of such a technique is as follows.

| HPLC: | Hewlett Packard Model 1100 w/Metatherm column heater | | | | |
|---|---|---|---|---|---|
| Column: | Waters Symmetry Shield RP$_8$; 4.6 mm × 250 mm (5 μm) | | | | |
| Column Temp.: | 40° C. | | | | |
| Flow: | 1.5 ml/min. | | | | |
| Wavelength: | 270 nm | | | | |
| Mobile Phase: | A) CH$_3$CN | | | | |
| | B) 95% 10 mM NH$_4$Ac pH = 5.0 (See below for prep.) 5% CH$_3$CN | | | | |
| Gradient Method: | 0.00 min. | 0% | A | 100% | B |
| | 5.00 min. | 0% | A | 100% | B |
| | 50.00 min. | 84.2% | A | 15.8% | B |
| | 55.00 min. | 0% | A | 100% | B |
| | 65.00 min. | 0% | A | 100% | B |

Mobile Phase Preparation:

50 mM NHAc: Weigh 3.85 g of NH$_4$Ac into a 1.0 L volumetric flask. Dilute to the mark with water. Stir until dissolved. Adjust pH to 5.0 with Acetic Acid. Filter through 0.45 μm nylon filter.

10 mM N$_4$Ac. Add 400 ml of 50 mM NH$_4$Ac to a 2.0 L volumetric flask. Dilute to the mark with water.

Sample Analysis: Weigh 10 mg of sample into a 10 ml volumetric flask. Add ~4 ml of DMF to the flask. Sonicate flask for 3 minutes. Dilute to the mark with DMF. Mix by inversion.

Example 2

In another example, for the determination of low levels (0.1-10 ppm) of the 2,3,7-triamino-4,6-dimethyl-1,9-phenazinedicarbonitrile impurity in certain precursors to 6-[(4,5-Dihydro-1H-imidazol-2-yl)amino-]-7-methyl-1H-benzimidazole-4-carbonitrile and its various salt forms, such as 7-cyano-5-amino-4-methyl-benzimidazole and formylated derivative and salt forms of each, one skilled in the art could employ the following equipment and conditions, or related systems, for reverse phase ion pairing HPLC/MS/MS with a stable-labeled, internal standard of the 2,3,7-triamino-4,6-dimethyl-1,9-phenazinedicarbonitrile impurity, such as $^{15}$N$_4$-2,3,7-triamino-4,6-dimethyl-1,9-phenazinedicarbonitrile (prepared as described in Example 4).

Instrument: HPLC system, such as a Gilson 305 pump with LEAP CTC PAL Autosampler, and a quadrapole mass spectrometer, such as a Sciex API4000 with Turbo Ion Spray Interface Column: A Waters Symmetry Shield $RP_{18}$, 2.1 mm×100 mm, 3.5 μm Mobile Phase: A gradient system comprised as follows Soln A: 10/90 MeOH/Water 2 mM Ammonium Acetate, 5 mM Heptafluorobutyric Acid Soln B: 90/10 MeOH/Water 2 mM Ammonium Acetate, 5 mM Heptafluorobutyric Acid

| Time (min) | Flow (mL/min) | % A | % B |
|---|---|---|---|
| initial | 0.5 | 70 | 30 |
| 2.0 | 0.5 | 70 | 30 |
| 6.0 | 0.5 | 0 | 100 |
| 7.0 | 0.5 | 0 | 100 |
| 7.1 | 0.5 | 70 | 30 |
| 8.0 | 0.5 | 70 | 30 |

For optimizing and calibrating the system, one skilled in the art would recognize appropriate approaches. For these operations, the artisan would recognize that the following samples would be useful: 7-cyano-5-amino-4-methyl-benzimidazole that is sufficiently free of the phenazine impurity (hereinafter referred to as Sample A), a relatively pure sample of the 2,3,7-triamino-4,6-dimethyl-1,9-phenazinedicarbonitrile impurity (hereinafter referred to as Sample B, prepared as described in Example 19), and a relatively pure sample of the stable-labelled 2,3,7-triamino-4,6-dimethyl-1,9-phenazinedicarbonitrile impurity (such as, $^{15}N_4$-2,3,7-triamino-4,6-dimethyl-1,9-phenazinedicarbonitrile, prepared as described in Example 4) to be used as an internal standard (hereinafter referred to as Sample C). The skilled artisan would likely prepare stock solutions of the Samples B and C in a suitable solvent, such as N,N-dimethylformamide.

One skilled in the art would recognize that the conditions for the operation of the mass spectrometer should be optimized prior to analysis. One skilled in the art might take the approaches described below for such optimization.

Q1 Optimization: A 250 μL syringe would be sequentially filled with solutions of Sample B and Sample C (~1.0 ng/μL) and infused at 30 μL/min. This flow would be introduced via a "T" shaped connector "teed-in" (post-column) with the column effluent at 570 μL/min. The mass spectrometer would be set for unit resolution, Q1 window set for m/z 200-500 scan range @ 1 ms dwell, and 0.1 step. The DP and EP, as well as other state file parameters for each compound, would be optimized using the "autotune feature" of the instrument. All other accessible parameters, needle position and gases would also individually optimized for sensitivity.

MS/MS Optimization: The $Q_1$ resolution would be set to nominal. The instrument would be set to daughter mode with $Q_3$ set to unit resolution, $Q_3$ window set for m/z 20-350 scan range. Collision energy would be optimized to yield daughter ions of sufficient intensity to be used for a multiple ion reaction monitoring detection scheme (hereinafter referred to as MRM).

The above optimization procedure might result in the following MS/MS conditions:

| | |
|---|---|
| Curtain gas | 10 |
| Ion Source Gas 1 (psi) | 68 |
| Ion Source Gas 2 (psi) | 60 |
| Ion Spray Voltage (ISV) | 1100 |
| CAD Gas: | 12 |
| Turbo Interface Temperature | 750° C. |
| Declustering Potential (DP) | 75 |
| Entrance Potential (EP) | 10 |
| Collision Energy (CE) | 43 |
| Collision Cell Exit Potential (CXP) | 21 |
| Scan Type: | MRM |
| 2,3,7-triamino-4,6-dimethyl-1,9-phenazinedicarbonitrile | m/z 304-277 |
| $^{15}N_4$-2,3,7-triamino-4,6-dimethyl-1,9-phenazinedicarbonitrile | m/z 308-280 |

For example, one skilled in the art may employ the following approach to calibration and sample preparation.

Calibration and Sample Prep: Calibration Range: 0.1-10 ppm

One skilled in the art would likely prepare each sample multiple times, such as triplicate, using the preparation scheme outlined below.

Stock solutions could be prepared as in the following table, appreciating techniques for serial dilutions.

Stock Solutions of Sample B

Weigh 1.47 mg and dissolve in about 1 mL DMF, and then prepare the following stock solutions:
Stock 1: 1058 pg/μL DMF
Stock 2: 105.8 pg/μL DMF
Stock 3: 10.58 pg/μL DMF Stock Solutions of Sample C Weigh 1.09 mg and dissolve in 1 about mL DMF, and then prepare the following stock solution.
Stock 4: 1090 pg/μL DMF Calibration Samples Internal Standard Blank Weigh 1 mg Sample A
Add 100 μL Stock 4
Sonicate for 10 min
Add 900 μL Mobile Phase A
Take a 50 μL sample of the above and dilute to 1 mL with Mobile Phase A Calibration Std 1 (0.1 ppm)
Weigh 1 mg Sample A
Add 10 μL Stock 3
Add 100 μL Stock 4
Sonicate 10 min
Add 890 μL Mobile Phase A
Take a 50 μL sample of the above and dilute to 1 mL with Mobile Phase A Calibration Std 2 (0.2 ppm)
Weigh 1 mg Sample A
Add 20 μL Stock 3
Add 100 μL Stock 4
Sonicate 10 min
Add 880 μL Mobile Phase A Take a 50 µL sample of the above and dilute to 1 mL with Mobile Phase A Calibration Std 3 (0.5 ppm)
  Weigh 1 mg Sample A
  Add 50 µL Stock 3
  Add 100 µL Stock 4
  Sonicate 10 min
  Add 850 µL Mobile Phase A
  Take a 50 µL sample of the above and dilute to 1 mL with Mobile Phase A Calibration Std 4 (1.0 ppm)
  Weigh 1 mg Sample A
  Add 10 µL Stock 2
  Add 100 µL Stock 4
  Sonicate 10 min
  Add 890 µL Mobile Phase A
  Take a 50 µL sample of the above and dilute to 1 mL with Mobile Phase A Calibration Std 5 (2.0 ppm)
  Weigh 1 mg Sample A
  Add 20 µL Stock 2
  Add 100 µL Stock 4
  Sonicate 10 min
  Add 880 µL Mobile Phase A
  Take a 50 µL sample of the above and dilute to 1 mL with Mobile Phase A Calibration Std 6 (5.0 ppm)
  Weighed 1 mg Sample A
  Add 50 µL Stock 2
  Add 100 µL Stock 4
  Sonicate 10 min
  Add 850 µL Mobile Phase A
  Take a 50 µL sample of the above and dilute to 1 mL with Mobile Phase A Calibration Std 7 (10.0 ppm)
  Weigh 1 mg Sample A
  Add 10 µL Stock 1
  Add 100 µL Stock 4
  Sonicate 10 min
  Add 890 µL Mobile Phase A
  Take a 50 µL sample of the above and dilute to 1 mL with Mobile Phase A Sample
  Weigh 1 mg sample
  Add 100 µL Stock 4
  Sonicate 10 min
  Add 900 µL Mobile Phase A
  Take a 50 µL sample of the above and dilute to 1 mL with Mobile Phase A Quantitation Procedure Quantitation could be achieved by applying instrument software, such as the "Quantitation" function of Analyst 1.2 software (residing on the API4000 data system) to the chromatographic MRM data acquired as prescribed above. Analyte:Internal Standard peak area ratios could be used to generate a standard analytical curve. Levels of 2,3,7-triamino-4,6-dimethyl-1,9-phenazinedicarbonitrile in unknown samples could then determined by first measuring analogous Analyte:Internal Standard ratios for each unknown sample, then referencing these versus the standard analytical curve. One skilled in the art would likely determine mean values for samples prepared by replicate analysis.

Example 3

For the determination of low (ppb) levels of the phenazine impurity in 6-[(4,5-Dihydro-1H-imidazol-2-yl)amino-]-7-methyl-1H-benzimidazole-4-carbonitrile and its various salt forms, one skilled in the art might employ reverse phase HPLC methodology with fluorescence detection. A suitable example is provided.

Instrument: An HPLC system that is equipped with an isocratic pump, injector, reverse phase HPLC column, column heater and fluorescence detector.

Column: A Waters Symmetry Shield $RP_{18}$, 4.6 mm×150 mm, 3.5 µm, held at 40° C.

Mobile Phase: A methanol:acetonitrile:phosphate/citrate buffer (2:3:5-v/v/v). The phosphate/citrate buffer is comprised of 20 mM $Na_2HPO_4$/5 mM citric acid, adjusted to pH 6.4 with 1N NaOH or $1:1H_3PO_4:H_2O$
  Flow Rate: 1.0 mL/min
  Excitation Wavelength: 450 nm
  Emission Wavelength: 570 nm
  Injection Volume: 200 µL Example 4

Synthesis of $^{15}N_4$-2,3,7-Triamino-4,6-dimethyl-1,9-phenazinedicarbonitrile (37) (A Stable Labeled Analog of Compound 2)

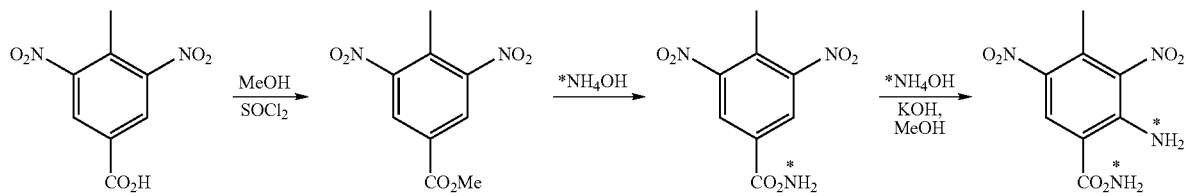

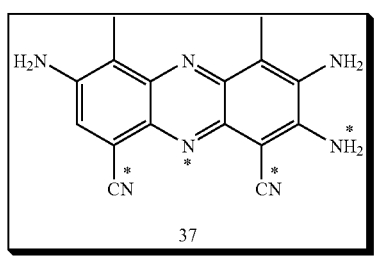 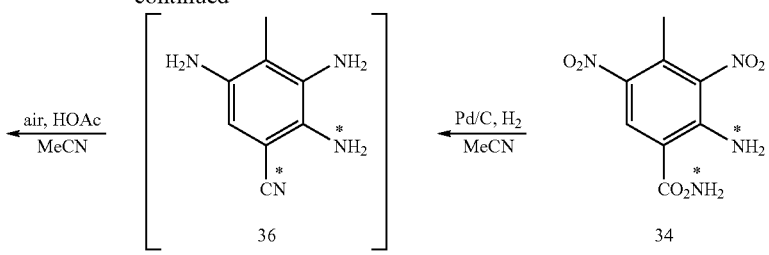

4-Methyl-3,5-dinitro-benzoic Acid, Methyl Ester (32)

To a mixture of 4-methyl-3,5-dinitro-benzoic acid (3) (35.1 g, 155 mmol) in anhydrous methanol (250 mL) is slowly added thionyl chloride (4 mL, 54 mmol). The resulting solution is heated to reflux for 16 hours. The solution is cooled to room temperature and then further cooled in an ice-water bath. The solid that forms is filtered and dried to give 4-methyl-3,5-dinitro-benzoic acid, methyl ester (32) (33.5 g, 139.5 mmol, 90% yield), as a white crystalline solid.

$^{15}$N-4-Methyl-3,5-dinitro-benzamide (33)

To a mixture of 4-methyl-3,5-dinitro-benzoic acid, methyl ester (32) (2.0 g, 8.3 mmol) in DMF (20 mL) is added 5.9 M $^{15}$N-ammonium hydroxide solution (5 g, 29.5 mmol). The reaction is then capped and stirred at room temperature for 48 hours. The reaction mixture is poured into a separatory funnel with methylene chloride (50 mL) and the resulting organic solution is extracted with water (50 mL). The organic portion is then dried over anhydrous sodium sulfate, filtered, and concentrated on a rotary evaporator to afford a tan solid which is purified by flash chromatography (silica, 35% ethyl acetate in hexanes) to provide $^{15}$N$_4$-methyl-3,5-dinitro-benzamide (33) (1.19 g, 5.3 mmol, 64% yield) as an off white solid.

$^{15}$N$_2$-2-Amino-4-methyl-3,5-dinitro-benzamide (34)

To a mixture of $^{15}$N-4-methyl-3,5-dinitro-benzamide (33) (1.0 g, 4.4 mmol) in methanol (50 mL) is added $^{15}$N-hydroxylamine hydrochloride (0.62 g, 8.8 mmol). The resulting mixture is stirred in an ice bath as a saturated solution of potassium hydroxide in methanol (5.5 mL) is added drop-wise, so as to maintain a reaction temperature near 15° C. After the addition is complete, the ice bath is removed and the reaction is allowed to stir at room temperature overnight. The pH of the reaction mixture is then adjusted to about 7 by the slow addition of acetic acid (about 1.2 mL). The reaction is then concentrated on a rotary evaporator and the resulting residue is resuspended in methanol (25 mL). The resulting mixture is stirred rapidly as water (125 mL) is added over several minutes. The mixture is then cooled in an ice bath for one hour and the solid obtained is filtered and dried to provide $^{15}$N$_2$-2-amino-4-methyl-3,5-dinitro-benzamide (34) (486 mgs, 2.0 mmol, 46% yield) as a brown solid.

$^{15}$N$_2$-2-Amino-4-methyl-3,5-dinitro-benzonitrile (35)

To a solution of $^{15}$N$_2$-2-amino-4-methyl-3,5-dinitro-benzamide (34) (470 mgs, 1.9 mmol) in anhydrous acetonitrile (3 mL) is slowly added phosphorous oxychloride (0.55 mL, 5.8 mmol, 3.0 equiv.). The mixture is then heated to reflux for 2.5 hours. The solution is then cooled to ambient temperature and water (3 mL) is slowly added over 20 minutes. The reaction mixture is stirred vigorously until solids begin to precipitate and then cooled in an ice water bath for 45 minutes. The resulting tan solid is filtered and dried to provide $^{15}$N$_2$-2-amino-4-methyl-3,5-dinitro-benzonitrile (35) (144 mg, 0.64 mmol, 34% yield).

$^{15}$N$_4$-2,3,7-Triamino-4,6-dimethyl-1,9-phenazinedicarbonitrile (37)

A mixture of $^{15}$N$_2$-2-amino-4-methyl-3,5-dinitro-benzonitrile (35) (144 mgs, 0.64 mmol), 10% Pd on carbon (30 mg) and acetonitrile (15 mL) is agitated under hydrogen pressure (40 psi) for 6 hours. The mixture is then filtered through a 0.45 micron filter disk, and the solution obtained is concentrated on a rotary evaporator. The residue obtained is placed under high vacuum to afford 114 mgs of triamine intermediate (36) as a dark brown solid. Acetonitrile (3 mL) and water (3 mL) are added to the solid, and then 0.5 N HCl is added until a pH of 4.8 is obtained. This solution is then heated to 40° C. and aerated for 7 hrs during which time solids precipitate. The mixture is cooled in an ice bath for 15 minutes and the solid obtained is filtered and dried to provide $^{15}$N$_4$-2,3,7-triamino-4,6-dimethyl-1,9-phenazinedicarbonitrile (37) (70 mg, 0.23 mmol, 36% over 2 steps), as a dark brown solid.

Example 5

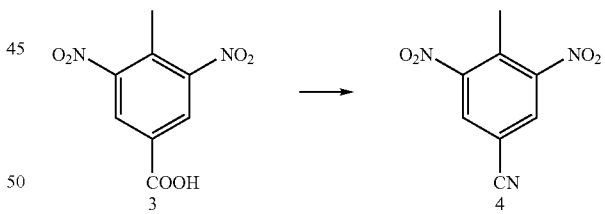

Preparation of 4-Methyl-3,5-dinitrobenzonitrile (4)

Phosphorus oxychloride (27.2 kg) is added over 30 minutes to a mixture of 4-methyl-3,5-dinitrobenzoic acid (3) (20.7 kg) and sulfamide (19.9 kg) in sulfolane (118 kg). The mixture is heated to about 120° C. and aged for about 8 hours. After cooling to ambient temperature, water (104 L) is added and the mixture is cooled to about 5° C. to crystallize the product. After aging at least 1.5 hours, the product is isolated via centrifugation, and washed with water (142 L). The product is then removed from the centrifuge and dried in a convection tray dryer at about 60° C. until drying is complete to provide 4-methyl-3,5-dinitrobenzonitrile (4) (17.3 kg, 91% yield) as a tan solid.

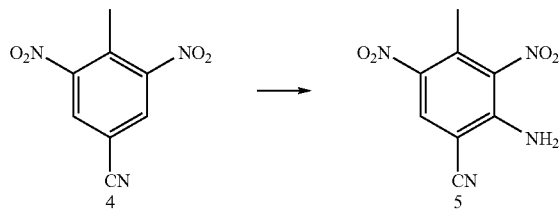

Preparation of 2-Amino-4-methyl-3,5-dinitrobenzonitrile (5)

A solution of 4-methyl-3,5-dinitrobenzonitrile (4) (10.5 kg), 4-amino-1,2,4-triazole (17.0 kg) and dimethyl sulfoxide (68.6 kg) is dosed into a mixture of lithium t-butoxide (12.2 kg) and dimethyl sulfoxide (106.6 kg) over about 50 minutes, while maintaining the temperature of each solution at about 20-25° C. After aging at about 20-25° C. for about 2 hours, acetic acid (8.9 kg) is dosed into the reaction mixture at about 20° C. over about 10 minutes. The product is crystallized by dosing water (158 L) into the reaction mixture over about 1.5 hours at about 20° C. The product slurry is cooled to about 10-15° C. and held at this temperature for about 45 minutes. The resultant slurry is filtered, and washed with water (106 L). The wet cake obtained is dried in a vacuum tray dryer at about 50° C. and 30 torr until drying is complete to provide 2-amino-4-methyl-3,5-dinitrobenzonitrile (5) (9.8 kg, 87% Yield) as an orange-brown solid.

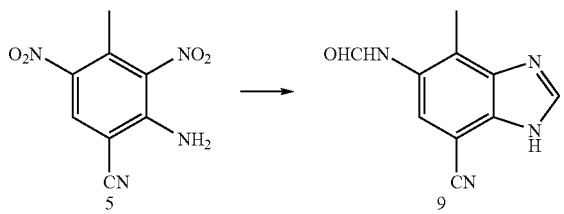

Preparation of 6-(Formylamino)-7-methyl-1H-benzimidazole-4-carbonitrile (9)

A mixture of platinum on carbon (sulfided) catalyst (5.3 kg of Engelhard C3759), formic acid (86.8 kg) and water (28.4 L) is heated to about 95° C. A mixture of 2-amino-4-methyl-3,5-dinitrobenzonitrile (5) (10.9 kg), formic acid (28 kg) and water (8 L) is then added to the catalyst-containing solution over about 45 minutes, while maintaining the temperature of the catalyst-containing mixture at about 95° C. The vessel that formerly contained the initial 2-amino-4-methyl-3,5-dinitrobenzonitrile/water/formic acid mixture is then rinsed with water (5.5 L) and the rinse solution is added to the catalyst-containing mixture. The resultant catalyst-containing mixture is then agitated at about 95° C. for about 30 minutes. After the mixture is cooled to about 35-45° C., the mixture is filtered to remove the catalyst and the filtered catalyst is washed with 96% formic acid (32.3 kg). The combined product-containing filtrate is placed under vacuum and heated (from about 25° C. to about 60° C.), and formic acid/water is distilled off, until about 98.4 kg of distillate is collected. At this point, methanol (109.1 kg) is added to the product-containing mixture. The mixture is gradually cooled to about 5° C., over a period of about 1 hour, and held at this temperature for about 1 hour. The mixture is then filtered and the product filter cake is washed with methanol (42.5 kg). The product is then dried in a vacuum tray dryer, at a temperature of about 45-50° C. and a vacuum of about 70 torr until dry to obtain 6-(Formylamino)-7-methyl-1H-benzimidazole-4-carbonitrile (9) (6.4 kg, 65% yield).

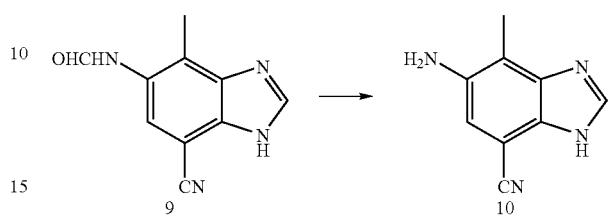

Preparation of 6-Amino-7-methyl-1H-benzimidazole-4-carbonitrile (10)

A mixture of 6-(Formylamino)-7-methyl-1H-benzimidazole-4-carbonitrile (9) (4.8 kg), water (46 L) and concentrated hydrochloric acid (17.8 kg) is agitated at about 80° C. for about 1½ hours. After the mixture is cooled to about 25° C., a solution of 50% aqueous sodium hydroxide (17.1 kg) and water (64 L) is added. The mixture is cooled to about 25° C. over about 15 minutes. The mixture is then filtered and the product is washed with water (50 L). The product is then dried in a vacuum tray dryer at 45-50° C. and ~40 torr until dry to obtain 6-Amino-7-methyl-1H-benzimidazole-4-carbonitrile (10) (3.8 kg, 94% yield).

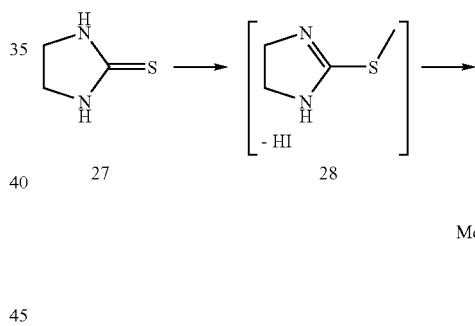

Preparation of 4,5-Dihydro-2-(methylthio)-1H-imidazole-1-carboxylic Acid, Methyl Ester (29)

Methyl iodide (39.1 kg) is dosed over about 30 minutes into a mixture of 2-imidazolidinethione (27) (20 kg) in absolute ethanol (120 kg). Additional absolute ethanol (9.8 kg) is then utilized to rinse the methyl iodidie transfer line into the reaction vessel. The solution is agitated at about 35° C. for about 50 minutes to form the 2-(methylthio)-2-imidazoline hydroiodide intermediate (28). Fine mesh potassium carbonate (40.6 kg) is added to the reactor and then methylchloroformate (20.3 kg) is added over about 30 minutes, while maintaining a reaction temperature of about 30-40° C. The mixture is agitated at about 40° C. for about 1 hour. The mixture is then heated to about 60° C. and filtered through a heated Nutsche filter to remove excess inorganic salts. The inorganic salt cake is washed with absolute ethanol (25.1 kg) and the combined product-containing solution is cooled to about −16° C. and held at this temperature for about 12 hours. The product is isolated via centrifugation, washed with water (about 30 L) and cold (about −20° C.) absolute ethanol (32.7 kg), and dried in a vacuum tray dryer at 60° C. and 100 torr, to provide 4,5-dihydro-2-(methylthio)-1H-imidazole-1-carboxylic acid, methyl ester (29) (22.6 kg, 66% yield).

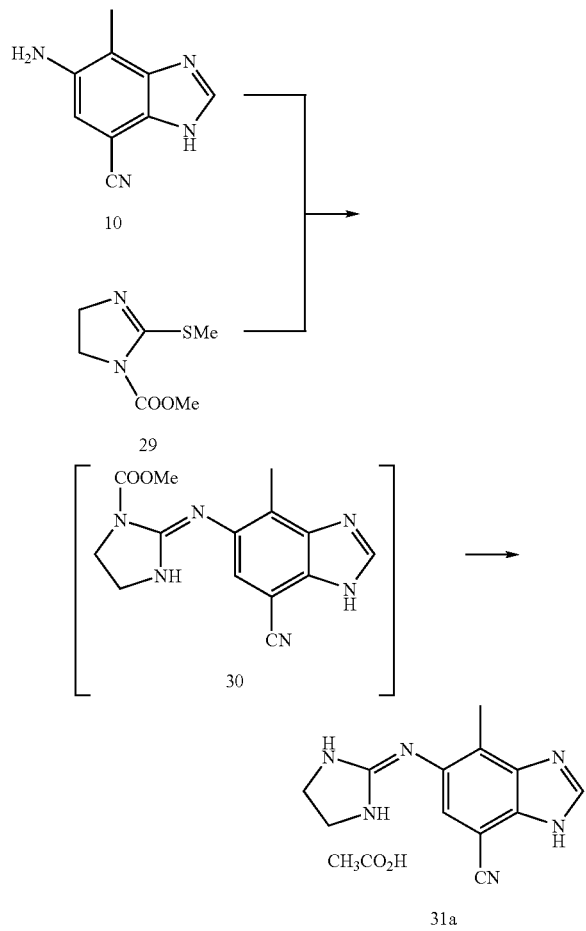

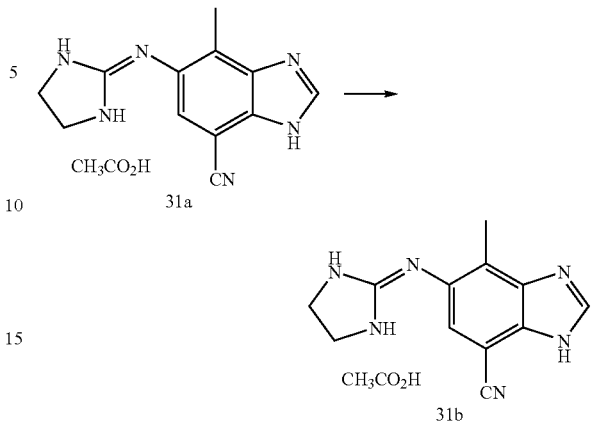

Preparation of Anhydrous 6-[(4,5-Dihydro-1H-imidazol-2-yl)amino-]-7-methyl-1H-benzimidazole-4-carbonitrile, Acetic Acid Salt (1:1) (31a)

A mixture of 6-Amino-7-methyl-1H-benzimidazole-4-carbonitrile (10) (3.9 kg), 4,5-dihydro-2-(methylthio)-1H-imidazole-1-carboxylic acid, methyl ester (29) (4.7 kg), acetic acid (11 kg) and acetonitrile (36.6 kg) is agitated at reflux (about 85° C.) for about 9 hours. Following reaction completion to intermediate product 30, n-propanol (22.8 kg) is added to the solution, and the reaction is agitated at reflux (~85° C.) for about 21 hours. The resulting product slurry is cooled to about 0° C. and held at this temperature for about 2 hours. The resultant slurry is filtered and the product obtained is washed with n-propanol (24.5 kg). The product is dried in a vacuum tray dryer, at a temperature of about 45-50° C. and a vacuum of about 10 torr until dry to obtain anhydrous 6-[(4,5-Dihydro-1H-imidazol-2-yl)amino-]-7-methyl-1H-benzimidazole-4-carbonitrile, acetic acid salt (1:1) (31a) (4.0 kg, 59% yield).

Recrystallization of Anhydrous 6-[(4,5-Dihydro-1H-imidazol-2-yl)amino-]-7-methyl-1H-benzimidazole -4-carbonitrile, Acetic Acid Salt (1:1) (31b)

A mixture of crude anhydrous 6-[(4,5-Dihydro-1H-imidazol-2-yl)amino-]-7-methyl-1H-benzimidazole-4-carbonitrile,acetic acid salt (1:1) (31a) (4.1 kg), activated carbon (1.2 kg, Darco G-60) and methanol (92.3 kg) is agitated at reflux (about 65° C.) for about 1 hour. The mixture is then cooled to about 40° C. and the activated carbon is removed via filtration. The product-containing filtrate is then heated to about 65° C. and methanol is distilled off until about 81L remains in the reaction vessel. As the distillation is continued, pre-heated (about 50-60° C.) acetonitrile (a total of about 130.5 kg) is then added at a rate to maintain a constant volume in the vessel, until a constant pot temperature is reached (about 84° C.). The resulting mixture is cooled to about 30° C. at a rate of about 1° C./minute, and then cooled to about 0° C. at a rate of about 0.5° C./minute. The mixture is then held at about 0° C. for about 11 hours and then the slurry is filtered. The product cake is washed with acetonitrile (about 23.7 kg). The product is then dried in a vacuum tray dryer, at a temperature of about 45-50° C. and a vacuum of about 10 torr for about 14 hours, to provide anhydrous 6-[(4,5-Dihydro-1H-imidazol-2-yl)amino-]-7-methyl-1H -benzimidazole-4-carbonitrile, acetic acid salt (1:1) (31b) (2.9 kg, 71% yield).

Example 6

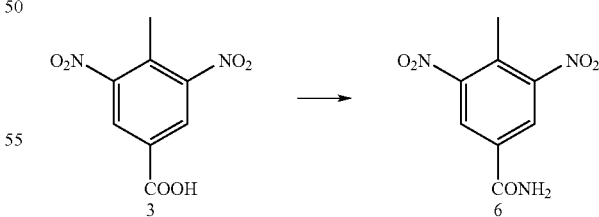

Preparation of 4-Methyl-3,5-dinitrobenzamide (6)

A mixture of 4-methyl-3,5-dinitrobenzoic acid (48.2 kg) (3) and sulfamide (50.1 kg) in pyridine (197 kg) is heated to reflux (about 115-120° C.) for about 1.5 hours. The solution is then cooled to ambient temperature and water is added (178 kg) over about 1 hour. The mixture is then cooled to about ~5° C. and held at this temperature for about 1 hour.

The product slurry is centrifuged and the solids obtained are washed with water (621 L). The product is dried in a vacuum tray dryer at a temperature of about 65° C. and a vacuum of about 10 torr to provide 4-methyl-3,5-dinitrobenzamide (6) (43.8 kg, 91.3% yield).

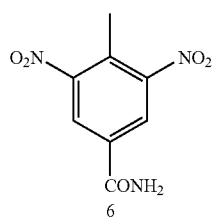

Preparation of 4-Methyl-3,5-dinitrobenzonitrile (4)

Phosphorus oxychloride (91.3 kg) is added over about 30 minutes into a mixture of 4-methyl-3,5-dinitrobenzamide (6) (66.6 kg) in acetonitrile (250.2 kg). The mixture is heated at reflux (about 80° C.) for about 2.5 hours. The solution is then cooled to ambient temperature and added to water (335 L) over about 1.5 hour, while maintaining a temperature of less than about 30° C. The mixture is cooled to about 5° C. and held at this temperature for about 18 hours. The product that precipitates is isolated via centrifugation, washed with water (469 L), and dried in a convection tray dryer at about 45° C. for about 22 hours to provide 4-methyl-3,5-dinitrobenzonitrile (4) (59 kg, 96% yield).

Example 7

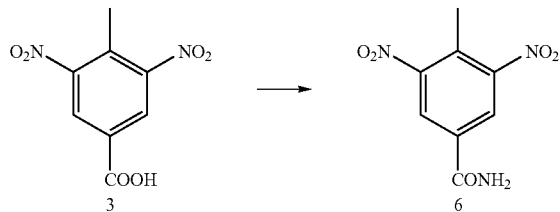

Preparation of 4-Methyl-3,5-dinitrobenzamide (6)

To a suspension of 4-methyl-3,5-dinitrobenzoic acid (3) (1.5 g) in acetonitrile (22.5 g, 30 mL) and triethylamine (0.87 g, 1.2 mL) at −10° C. is slowly added a solution of methylchloroformate (0.723 g, 0.6 m-L) in acetonitrile (2.25 g, 3 mL). The resulting mixture is agitated at −10° C. for about 1 hour, whereupon ammonia gas (excess) is bubbled though the mixture for about 30 minutes. The resultant mixture is allowed to age at about −5 to −10° C. for 12 hours, whereupon the mixture is added to a mixture of ice and water (100 mL). The solid that precipitates is filtered and dried to provide 4-methyl-3,5-dinitrobenzamide (6) (1.36 g, 91% Yield).

Example 8

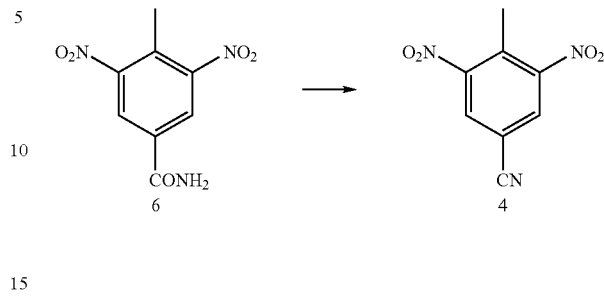

Preparation of 4-Methyl-3,5-dinitrobenzonitrile (4)

Phosphorus pentachloride (1.082 g) is added over about 30 minutes into a mixture of 4-methyl-3,5-dinitrobenzamide (6) (1.04 g) in acetonitrile (20 mL, 15 g). The mixture is then heated to about 60° C. for about 4 hours. The solution is then cooled to ambient temperature and is slowly added to an ice and water mixture (20 mL). The mixture is cooled to about 5° C., whereupon ammonium hydroxide is added until a pH of about 8 is attained. The product that precipitates is filtered, washed with water (10 mL), and dried to provide 4-methyl-3,5-dinitrobenzonitrile (4) (0.72 g, 75% Yield).

Example 9

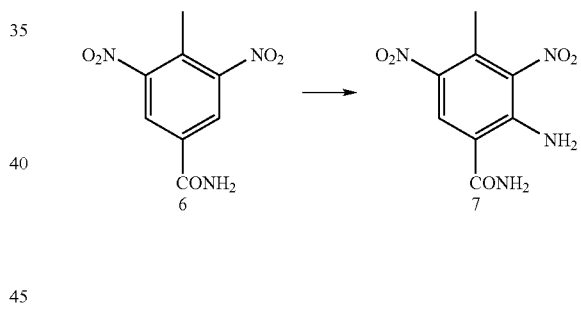

Preparation of 2-Amino-4-methyl-3,5-dinitrobenzamide (7)

A solution of 4-methyl-3,5-dinitrobenzamide (6) (15.1 kg) in dimethyl sulfoxide (95.6 kg) is added to a solution of 4-amino-1,2,4-triazole (21.6 kg) and potassium tert-butoxide (21.7 kg) in dimethyl sulfoxide (144.5 kg) at a rate to maintain a temperature of about 20° C. The mixture is allowed to stir for about 30 minutes, whereupon additional amounts of 4-amino-1,2,4-triazole (5.5 kg) and potassium tert-butoxide (3.7 kg) are added. The mixture is allowed to stir for about 1 hour at about 20° C., and then the mixture is added, over a period of about 30 minutes, to a cold (about 5° C.) solution of water (347 kg) and acetic acid (15 kg), allowing the temperature to rise to about 25° C. The vessel containing the initial reaction mixture is then rinsed with water (87 kg) and the rinse solution is also added to the acetic acid solution. The resulting mixture is cooled to about 5° C. and held at this temperature for about 30 minutes, whereupon the mixture is filtered and the solids obtained are washed with water (82 kg). The solids are then dried in a vacuum tray dryer for about 19 hours, at a temperature of about 50° C. and a vacuum of about 15 torr, to provide 2-amino-4-methyl-3,5-dinitrobenzamide (7) (13.6 kg, 84% yield).

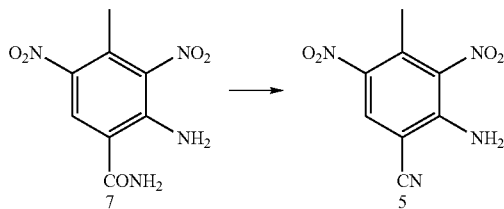

Preparation of 2-Amino-4-methyl-3,5-dinitrobenzonitrile (5)

To a mixture of 2-amino-4-methyl-3,5-dinitrobenzamide (7) (12.5 kg) in acetonitrile (78.4 kg) is added phosphorus oxychloride (14.8 kg) over a period of about 35 minutes. The mixture is then heated to reflux. After approximately 3.25 hours, the mixture is cooled to about 25° C. and added to water (245 kg). The vessel that formerly contained the reaction mixture is rinsed with acetonitrile (16 kg) and the rinse solution is also added to the aforementioned water quench solution. The quench solution is then cooled to about 5° C. over a period of about 2 hours. The quench solution is then filtered, the vessel that formerly contained the quench solution is rinsed with water (93 kg), and the rinse solution is passed through the product-containing filter. The product obtained is then dried in a vacuum tray drier, at a temperature of about 47° C. and a vacuum of about 12 torr, to provide 2-amino-4-methyl-3,5-dinitrobenzonitrile (5) (9.6 kg, 83.5% yield).

Example 10

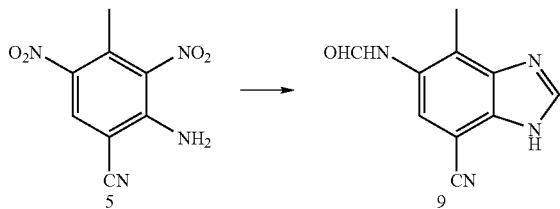

Preparation of 6-(Formylamino)-7-methyl-1H-benzimidazole-4-carbonitrile (9)

A mixture of 2-amino-4-methyl-3,5-dinitrobenzonitrile (5) (22.2 g), 5% platinum on carbon (sulfided) catalyst (2.2 g, 57.8% moisture content, Engelhard-Rome, Italy, 43045), 5% platinum on carbon with 1% vanadium (1.22 g, 61.74% moisture content, Degussa, CF 1082 XBA/W) and 80% aqueous formic acid (328 g) is heated to about 90° C., over about 50 minutes. The resultant catalyst-containing mixture is then agitated at about 90-93° C. for about 2 hours. The mixture is then cooled to about 25° C. and filtered through Celite to remove the catalyst. The filter cake is washed with 80% aqueous formic acid (50 g), and the combined product-containing filtrate (about 377 g) is placed under vacuum (about 30 mbar) and heated (45° C.), and formic acid/water is distilled off, until about 150 g of the product-containing mixture remains. Methanol (about 150 mL) is added to the product-containing mixture at a temperature of about 45° C.

After holding the mixture at a temperature of about 45° C. for about 15 minutes, the mixture is gradually cooled to about 0° C., over a period of about 30 minutes, and held at this temperature for about 1 hour. The mixture is then filtered and the product filter cake is washed with methanol (about 74 mL). The product is then dried, at a temperature of about 45-50° C. and a vacuum of about 25 mbar, to obtain 6-(Formylamino)-7-methyl-1H-benzimidazole-4-carbonitrile (9) (15.3 g, 76% Yield).

Example 11

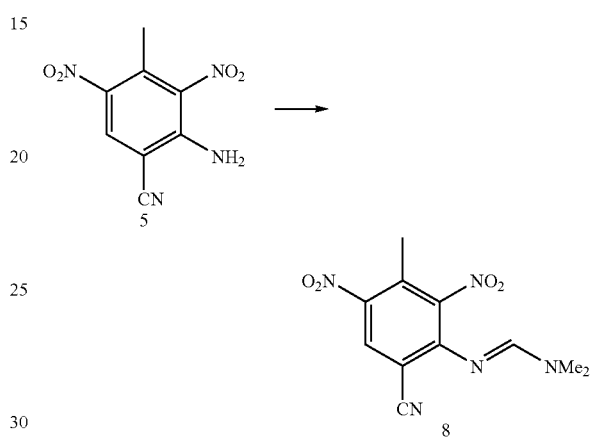

Preparation of N'-(6-Cyano-3-methyl-2,4-dinitro-phenyl)-N,N-dimethyl-methanimidamide (8)

To a suspension of 2-amino-4-methyl-3,5-dinitrobenzonitrile (5) (3.129 g, 14.1 mmol) in anhydrous toluene is added N,N-dimethylformamide dimethyl acetal (4 mL). The resultant mixture is heated to about 100° C. for about 2.5 hours. The mixture is cooled to ambient temperature and the solvent is removed using a rotary evaporator. The residue is dried to provide crude N'-(6-Cyano-3-methyl-2,4-dinitro-phenyl)-N,N-dimethyl-methanimidamide (8) (3.85 g, 99% Yield) as a red solid.

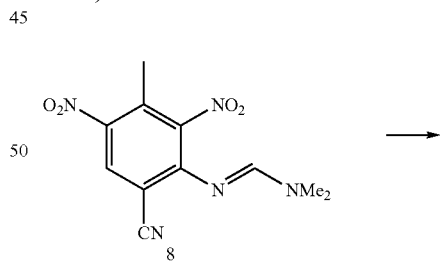

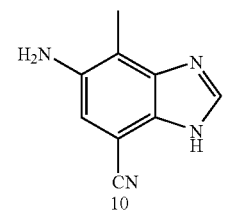

Preparation of 6-Amino-7-methyl-1H-benzimidazole-4-carbonitrile (10)

A mixture of N'-(6-cyano-3-methyl-2,4-dinitro-phenyl)-N,N-dimethyl-methanimidamide (8) (0.607 g, 2.42 mmol) and 10% palladium on carbon (0.23 g of 50% water wet) and methanol (60 mL) is agitated under hydrogen pressure (43 psi) for about 4.5 hours. The vessel is then flushed with nitrogen and the mixture is heated to 60° C. for about 2.5 hours. The mixture is allowed to cool to ambient temperature and is then filtered through a pad of Celite. The solvent is then evaporated in vacuo to provide 6-Amino-7-methyl-1H-benzimidazole-4-carbonitrile (10) (0.426 g, >100% crude Yield), as a brown solid.

Example 12

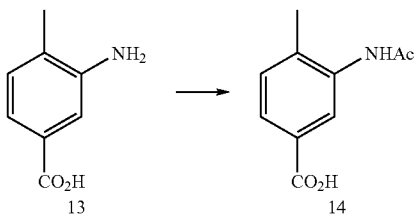

Preparation of 3-(Acetylamino)-4-methylbenzoic Acid (14)

A mixture of 3-amino-4-methylbenzoic acid (13) (27.23 g, 180.2 mmol) and acetic acid (190 mL) is heated to 60° C., and acetic anhydride (120 mL, 1300 mmol) is introduced to the reaction mixture over about 0.25 hours. The reaction mixture is then heated to reflux and stirred for about 30 minutes. The mixture is then cooled to room temperature, and the solid obtained is filtered, washed with water (100 mL), and dried to provide 3-(Acetylamino)-4-methylbenzoic Acid (14) as a light pink colored solid (26.37 g, 76% Yield).

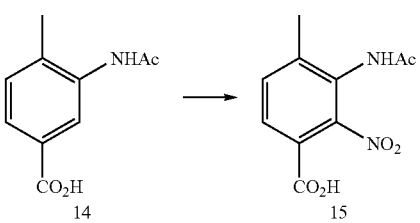

Preparation of 3-(Acetylamino)-4-methyl-2-nitrobenzoic Acid (15)

Fuming nitric acid (100 mL, 2.4 mol) is cooled to about 0° C. (ice/acetone/water bath) and 3-(Acetylamino)-4-methylbenzoic Acid (14) (24.567 g, 127.2 mmol) is added in small portions over about 30 minutes, at rate to maintain the internal reaction temperature <5° C. The hetereogeneous reaction mixture is then stirred at about 0° C. for an additional 1 hour. The reaction mixture is then added to ice water (300 mL) and stirred for about 1 hour. The solid obtained is filtered and dried to provide a mixture of 3-N-acetyl-4-methyl-2-nitro benzoic acid (5) and 3-N-acetyl-4-methyl-5-nitro benzoic acid, in ratio of about 78:22 (27.79 g, 92% Combined Yield). A portion of this mixture (23.458 g) is recrystallized from acetic acid (300 mL) to give 3-(Acetylamino)-4-methyl-2-nitrobenzoic Acid (15), as a white solid (15.370 g, 51% yield).

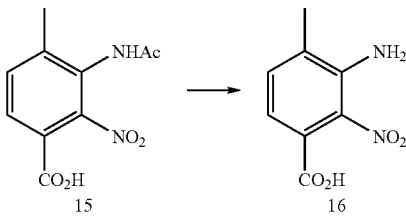

Preparation of 3-Amino-4-methyl-2-nitrobenzoic Acid (16)

To a 70% aqueous solution of $H_2SO_4$ (100 mL) is added 3-(Acetylamino)-4-methyl-2-nitrobenzoic Acid (15) (14.30 g, 60.00 mmol), and the reaction mixture heated to about 115° C. for about 30 minutes. The mixture is then cooled to ambient temperature, added to ice water (250 mL) and held at about 0° C. for about 30 minutes. The resulting solid is filtered, washed with water (100 mL), and dried to provide 3-amino-4-methyl-2-nitrobenzoic acid (16) as a rust colored solid (7.17 g, 61% yield).

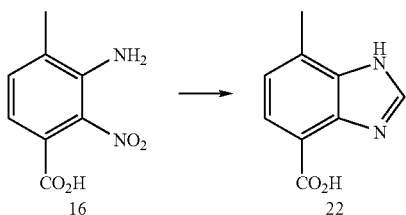

Preparation of 7-Methyl-1H-benzimidazole-4-carboxylic Acid (22)

A mixture of 3-amino-4-methyl-2-nitrobenzoic acid (16) (6.883 g, 35.10 mmol), 10% Pd/C [0.3 g, 10% dry Pd/C] and 75% aqueous formic acid (60 mL) is heated to reflux for about 15 hours. The reaction mixture is then cooled to ambient temperature and filtered through a pad of Celite, and the resulting filtrate concentrated in vacuo to a beige solid. The solids are triturated in hot methanol (50 mL), cooled slowly to ambient temperature, and filtered to give 7-Methyl-1H-benzimidazole-4-carboxylic Acid (22), as beige solid (5.26 g, 85% Yield).

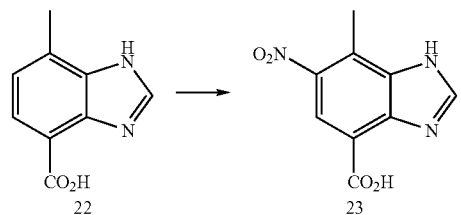

Preparation of 7-Methyl-6-nitro-1H-benzimidazole-4-carboxylic Acid (23)

A mixture of 7-Methyl-1H-benzimidazole-4-carboxylic Acid (22) (4.944 g, 28.10 mmol) and concentrated $H_2SO_4$ (30 mL) is heated to about 60° C. to obtain a solution which is then cooled to about 0° C. To this solution is added KNO₃ (3.12 g, 30.9 mmol) portionwise, so as to maintain the internal reaction temperature <10° C. Following complete addition, the cooling source is removed and the reaction mixture is allowed to warm to ambient temperature, whereupon the mixture is stirred for about 1 hour. The reaction mixture is then added to ice water (100 mL) and held at about 0° C. for about 4 hours. The resulting solids are filtered, washed with water, and dried to provide 7-Methyl-6-nitro-1H-benzimidazole-4-carboxylic Acid (23) as an off white solid (6.12 g, 98% yield).

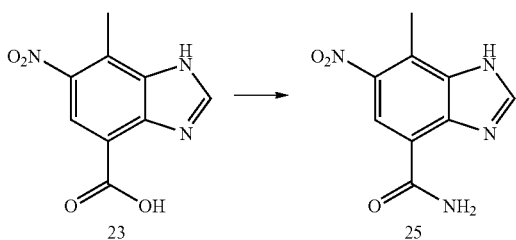

Preparation of 7-Methyl-6-nitro-1H-benzimidazole-4-carboxamide (25)

A mixture of 7-Methyl-6-nitro-1H-benzimidazole-4-carboxylic Acid (23) (0.692 g, 3.12 mmol), sulfamide (0.600 g, 6.26 mmol), and pyridine (8 mL) is heated at reflux for about 16 hours. The resulting heterogeneous reaction mixture is cooled to ambient temperature, diluted with water (10 mL) and cooled to 0° C. for 1 hour. The solids that form are filtered, washed with water (10 mL) and methanol (10 mL), and dried to obtain 7-Methyl-6-nitro-1H-benzimidazole-4-carboxamide (25) as a cream colored solid (0.586 g, 85% yield).

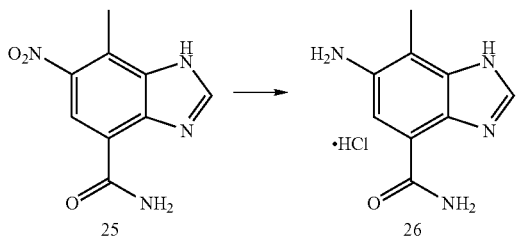

Preparation of 6-Amino-7-Methyl-1H-benzimidazole-4-carboxamide, Hydrochloric Acid Salt (26)

A suspension of 7-Methyl-6-nitro-1H-benzimidazole-4-carboxamide (25) (0.533 g, 2.42 mmol), Pd/C (10% Pd/C, 0.07 g), 1M aqueous HCl (15 mL) and methanol (4 mL) is hydrogenated at 40 psi hydrogen pressure for about 3 hours. When hydrogen uptake has ceased, the reaction mixture is filtered through a Celite pad and the filtrate is concentrated in vacuo to a white solid. The white solid is recrystallized from ethanol/water (3/1 v/v) to provide 6-Amino-7-Methyl-1H-benzimidazole-4-carboxamide, hydrochloric acid salt (26) as a white solid (0.421 g, 77% yield).

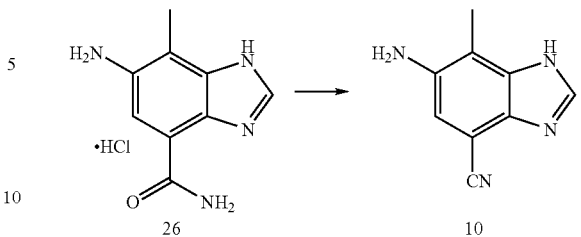

Preparation of 6-Amino-7-Methyl-1H-benzimidazole-4-carbonitrile (10)

A suspension of 6-Amino-7-Methyl-1H-benzimidazole-4-carboxamide, hydrochloric acid salt (26) (0.425 g, 1.88 mmol), in POCl₃ (3 mL, 32.2 mmol), and DMF (about 2 drops) is heated at reflux for about 2 hours. The reaction mixture is cooled to ambient temperature, the POCl₃ is removed in vacuo, and the solids obtained are dissolved in water (10 mL) and stirred for about 1 hour. Saturated NH₄OH is added to the resulting aqueous solution until a pH of about 8 is attained. The mixture is chilled overnight and the solids obtained are filtered to provide 6-Amino-7-Methyl-1H-benzimidazole-4-carbonitrile (10) as a light yellow solid (0.226 g, 70% yield).

Example 13

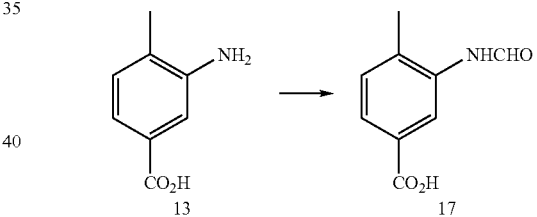

Preparation of 3-(Formylamino)-4-methylbenzoic Acid (17)

A mixture of 3-amino-4-methylbenzoic acid (13) (22.139 g, 146.5 mmol) and 90% aqueous formic acid (200 mL) is heated at reflux for about 2 hours. The mixture is cooled to ambient temperature, added to ice water (400 mL) and stirred for about 15 minutes. The solids obtained are filtered and dried to obtain 3-(formylamino)-4-methylbenzoic acid (17), as a light flaky purple-pink solid (23.213 g, 88% yield).

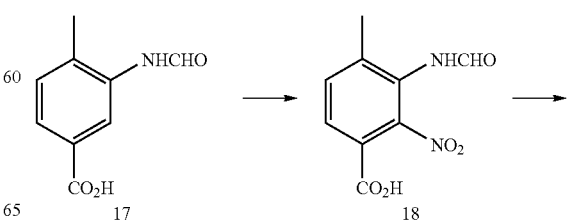

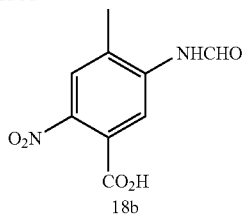

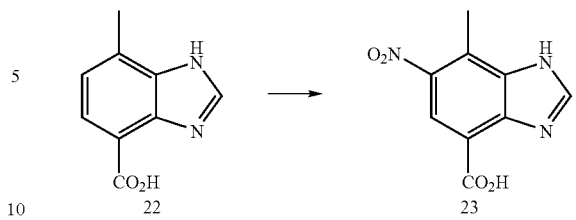

Preparation of 3-(Formylamino)-4-methyl-2-nitrobenzoic acid (18)

Fuming nitric acid (70 mL) is cooled about 0° C. and 3-(formylamino)-4-methylbenzoic acid (17) (18.630 g, 103.9 mmol) is added in small portions over about 45 minutes, at such a rate to maintain the internal reaction temperature <5° C. The homogeneous reaction mixture is stirred at about 0° C. for an additional 1 hour. The reaction mixture is the added to ice water (300 mL) and stirred for about 1 hour. The solids that form are filtered and dried to provide a mixture of 3-(Formylamino)-4-methyl-2-nitrobenzoic acid (18) and 3-(Formylamino)-4-methyl-6-nitrobenzoic acid (18b) in a ratio of about 66:34 (21.188 g, 91% Combined Yield).

Preparation of 7-Methyl-6-nitro-1H-benzimidazole-4-carboxylic Acid (23)

A mixture of 7-Methyl-1H-benzimidazole-4-carboxylic Acid (22) (4.944 g, 28.10 mmol) and concentrated $H_2SO_4$ (30 mL) is heated to about 60° C. to obtain a solution which is then cooled to about 0° C. To this solution is added $KNO_3$ (3.12 g, 30.9 mmol) portionwise, so as to maintain the internal reaction temperature <10° C. Following complete addition, the cooling source is removed and the reaction mixture is allowed to warm to ambient temperature, whereupon the mixture is stirred for about 1 hour. The reaction mixture is then added to ice water (100 mL) and held at about 0° C. for about 4 hours. The resulting solids are filtered, washed with water, and dried to provide 7-Methyl-6-nitro-1H-benzimidazole-4-carboxylic Acid (23) as an off white solid (6.12 g, 98% Yield).

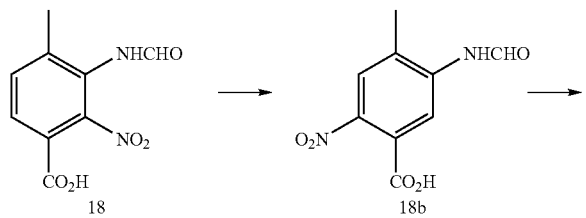

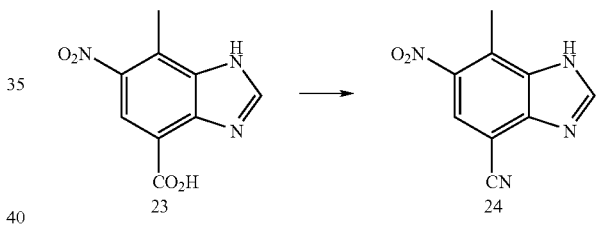

Preparation of 7-Methyl-1H-benzimidazole-4-carboxylic Acid (22)

A mixture of 3-(Formylamino)-4-methyl-2-nitrobenzoic acid (18) and 3-(Formylamino)-4-methyl-6-nitrobenzoic acid (18b) in a ratio of about 66:34 (9.999 g, 44.56 mmol) and Pd/C (10%, 2 g, 4 mol % Pd) in 75% aqueous formic acid (120 mL, 0.5M) is heated at reflux for about 15 hours. The reaction mixture is then cooled to ambient temperature and filtered through a pad of Celite, and the filtrate is concentrated in vacuo to a beige solid. The solids are triturated in hot methanol (50 mL), cooled slowly to ambient temperature, and filtered to give 7-Methyl-1H-benzimidazole-4-carboxylic Acid (22) as beige solid (5.564 g, 98% Yield, based on amount of 3-(Formylamino)-4-methyl-2-nitrobenzoic acid (18) in the starting material mixture).

Preparation of 7-Methyl-6-nitro-1H-benzimidazole-4-carbonitrile (24)

A mixture of 7-Methyl-6-nitro-1H-benzimidazole-4-carboxylic Acid (23) (16.99 g, 76.90 mmol), $POCl_3$ (15.76 mL, 169 mmol), and sulfamide (14.767 g, 154 mmol) in sulfolane (77 mL) is heated to about 120° C. for about 3 hours. The reaction mixture is cooled to ambient temperature and added to ice water (1 L). The resultant mixture is cooled to about 0° C. filtered to provide 7-Methyl-6-nitro-1H-benzimidazole-4-carbonitrile (24), as an off white solid (12.54 g, 80% Yield).

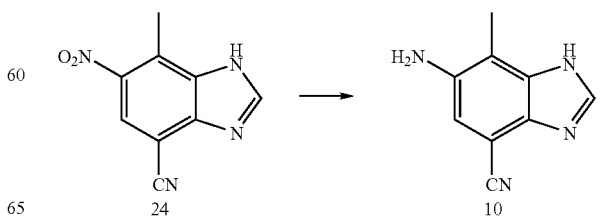

Preparation of 6-Amino-7-methyl-1H-benzimidazole-4-carbonitrile (10)

A mixture of 7-Methyl-6-nitro-1H-benzimidazole-4-carbonitrile (24) (1.010 g, 5.0 mmol) and Pt/C (5% Pt/C sulfided, 0.502 g, 50 wt %, C5002 Engelhard Industries) in DMF (75 mL) is hydrogenated at about 40 psi hydrogen pressure at about 50° C. over about 24 hours. The catalyst is removed from the reaction mixture by filtration through a Celite pad and the filtrate is concentrated in vacuo. The residue obtained is triturated in acetonitrile, and filtered to provide 6-Amino-7-methyl-1H-benzimidazole-4-carbonitrile (10), as a tan solid (0.768 g, 90% Yield).

Example 14

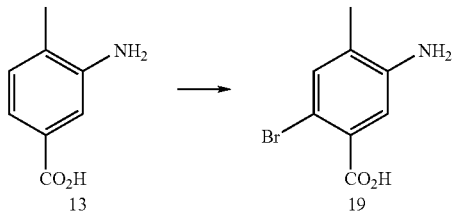

Preparation of 3-Amino-6-bromo-4-methylbenzoic Acid (19)

A mixture of 3-amino-4-methylbenzoic acid (13) (5.1525 g, 34.08 mmol)) and DMF (30 mL) is cooled to about 5° C., whereupon N-bromosuccinimide (6.230 g, 35 mmol) is added in small portions, at a rate such that the reaction temperature stays below 10° C. The reaction mixture is then stirred at ambient temperature for about 3 hours and is then added to ice water (150 mL). The solids that form are filtered and dried to provide 3-Amino-6-bromo-4-methylbenzoic Acid (19) (6.5439 g, 83% yield).

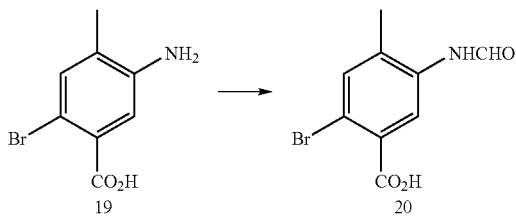

Preparation of 3-(Formylamino)-6-bromo-4-methylbenzoic Acid (20)

A mixture of 3-Amino-6-bromo-4-methylbenzoic Acid (19) (6.4145 g, 27.88 mmol) in 90% aqueous formic acid (36 mL) is heated to reflux for about 3 hours. The mixture is then cooled to ambient temperature, added to ice water (150 mL) and stirred for about 15 minutes. The solids that form are filtered and dried to provide 3-(Formylamino)-6-bromo-4-methylbenzoic Acid (20):, as a purple-pink solid (5.961 g, 82% Yield).

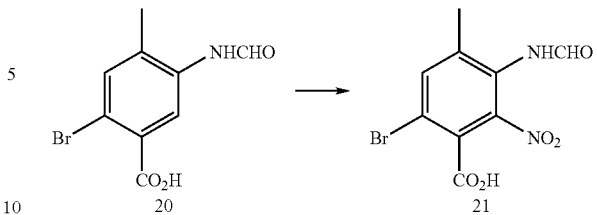

Preparation of 3-(Formylamino)-6-bromo-4-methyl-2-nitrobenzoic Acid (21)

Fuming nitric acid (120 mL, 2.8 mol) is cooled to about 0° C., whereupon 3-(Formylamino)-6-bromo-4-methylbenzoic Acid (20) (28.243 g, 109.5 mmol) is added in small portions over about 45 minutes, at such a rate to maintain the internal reaction temperature <5° C. The reaction mixture is then stirred at about 0° C. for about 1 hour. The reaction mixture is added to ice water (500 mL) and stirred for about 1 hour. The solids that form are filtered and dried to provide 3-(Formylamino)-6-bromo-4-methyl-2-nitrobenzoic Acid (21), as a beige powder (31.465 g, 95% yield).

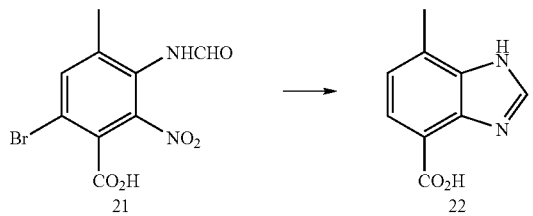

Preparation of 7-Methyl-1H-benzimidazole-4-carboxylic Acid (22)

A mixture of 3-(Formylamino)-6-bromo-4-methyl-2-nitrobenzoic Acid (21) (1.055 g, 3.68 mmol) and palladium on carbon (10% Pd/C, 0.228 g) in aqueous NaOH (0.294 g, 7.35 mmol of solid NaOH in 100 mL of $H_2O$) is hydrogenated under hydrogen pressure (40 psi) for about 16 hours. The reaction mixture is cooled to ambient temperature and filtered through a pad of Celite. The filtrate is acidified with $HCO_2H$ (about 25 mL) and heated to reflux for about 2 hours. The reaction mixture is cooled and concentrated in vacuo to give a beige solid. The solids are triturated in hot methanol (50 mL), cooled slowly to ambient temperature, and filtered to give 7-Methyl-1H-benzimidazole-4-carboxylic Acid (22), as beige solid (0.495 g, 81% yield).

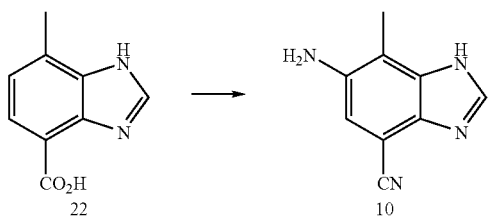

Preparation of 6-Amino-7-methyl-1H-benzimidazole-4-carbonitrile (10)

7-Methyl-1H-benzimidazole-4-carboxylic Acid (22) is converted to 6-Amino-7-methyl-1H-benzimidazol-4-carbonitrile (10), as described in Example 13.

Example 15

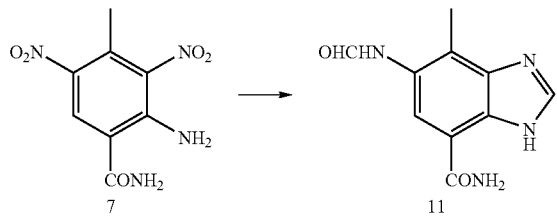

Preparation of 6-(Formylamino)-7-methyl-1H-benzimidazole-4-carboxamide (11)

A mixture of 1-amino-4-methyl-3,5-dinitrobenzamide (7) (0.5 g, 2.08 mmol), 80% aqueous formic acid (7.5 mL), and 5% palladium on carbon (0.2 g, ESCAT 160, Engelhard) is heated to about 90° C. for about 1 hour. The mixture is then cooled to ambient temperature and filtered through Celite. The filter cake is washed with 80% aqueous formic acid (1 mL) and the combined filtrate is concentrated in vacuo. The residue obtained is dissolved in water (10 mL) and $NH_4OH$ is added until a pH of about 9 is attained. The solution is cooled to about 5° C. and held overnight. The solids that form are filtered and dried to obtain 6-(Formylamino)-7-methyl-1H-benzimidazole-4-carboxamide (11) (0.383 g, 84% yield), as a tan solid.

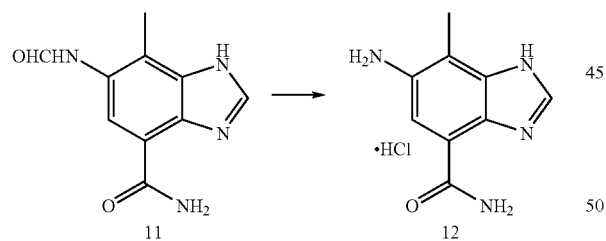

Preparation of 6-(Amino)-7-methyl-1H-benzimidazole-4-carboxamide, Hydrochloric Acid Salt (12)

A mixture of 6-(Formylamino)-7-methyl-1H-benzimidazole-4-carboxamide (11) (0.35 g, 1.6 mmol), 1M aqueous HCl (10 mL) and methanol (3 mL) is heated to reflux for about 1 hour. The reaction mixture is allowed to cool to ambient temperature and is then concentrated in vacuo to a white solid. The white solid is recrystallized from ethanol/water (3/1 v/v) to provide 6-(Amino)-7-methyl-1H-benzimidazole-4-carboxamide; hydrochloric acid salt (12) as a white solid (0.164 g, 54% Yield).

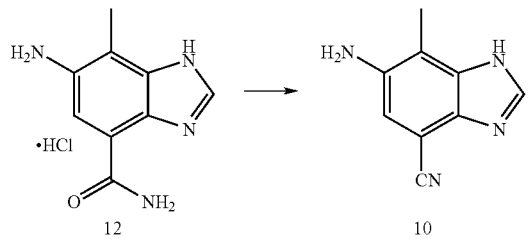

Preparation of 6-Amino-7-methyl-1H-benzimidazole-4-carbonitrile (10)
6-(Amino)-7-methyl-1H-benzimidazole-4-carboxamide, hydrochloric acid salt (12) is converted to 4-methyl-5-amino-7-cyano-benzimidazole (10), as described in Example 12.

Example 16

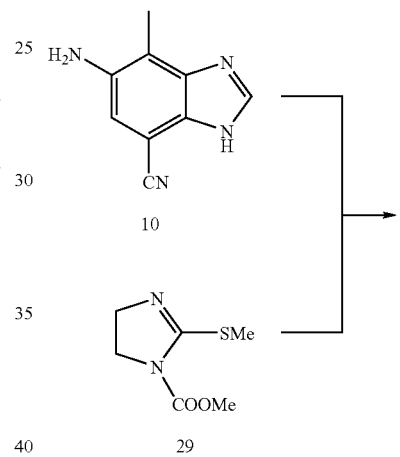

Preparation of 2-(7-Cyano-4-methyl-1H-benzimidazol-5-yl-imino)-imidazolidine-1-carboxylic Acid Methyl Ester (30)

A mixture of 6-Amino-7-methyl-1H-benzimidazole-4-carbonitrile (10) (22.3 g, 0.13 mol), 4,5-dihydro-2-(methylthio)-1H-imidazole-1-carboxylic acid, methyl ester (29) (27.1 g, 0.155 mol) and glacial acetic acid (223 mL) is heated to about 85° C. for about 3 hours. The reaction mixture is allowed to cool to ambient temperature and is then concentrated in vacuo. At ambient temperature, water (223 mL) is then added to the oily residue obtained, and the pH of the resultant solution is adjusted to about 8.1 with 6N aqueous NaOH. The solids that formed are filtered, washed with water (75 mL), and dried to provide 2-(7-Cyano-4-methyl-1H-benzimidazol-5-yl-imino)-imidazolidine-1-carboxylic Acid Methyl Ester (30) (29.1 g, 75% Yield), as an off-white solid.

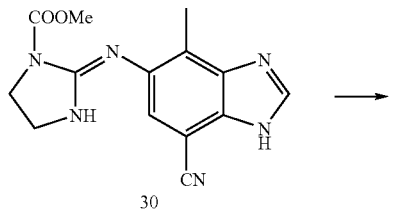

Preparation of 6-[(4,5-Dihydro-1H-imidazol-2-yl)amino-]-7-methyl-1H-benzimidazole-4-carbonitrile, Acetic Acid Salt (1:1) (31a)

A mixture of 2-(7-Cyano-4-methyl-1H-benzimidazol-5-yl-imino)-imidazolidine-1-carboxylic Acid Methyl Ester (30) (1.0 g, 3.35 mmol), methanol (30 mL), and acetic acid (0.2 mL) is heated to reflux for about 16 hours. Activated carbon (1 g) is then added and heating is continued for about 30 minutes. The hot mixture is then filtered through a pad of Celite and the filter cake is washed with hot methanol (5 mL). The filtrates are combined and heated to distill off methanol, until the solution becomes cloudy, whereupon acetonitrile (100 mL) is added and distillation is continued, until the methanol has been displaced, as indicated by a rise in the temperature of the distillation head. The mixture is then cooled to ambient temperature and allowed to stir for about 1 hour. The solids that form are filtered, washed with acetonitrile (5 mL), and dried to provide N-(4,5-dihydro-1H-imidazol-2-yl)-7-cyano-4-methyl-1H-benzimidazol-5-amine, acetic acid salt (1:1) (31a) (0.71 g, 71% Yield), as a yellowish white solid.

Example 17

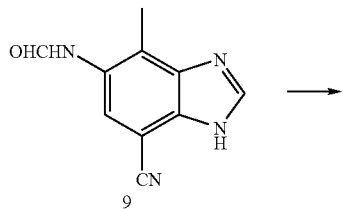

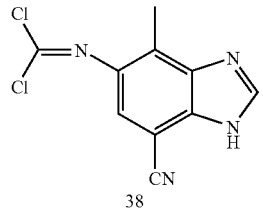

Preparation of 6-[(Dichloromethylene)amino]-7-methyl-1H-benzimidazole-4-carbonitrile (38)

6-Formylamino-7-methyl-1H-benzimidazole-4-carbonitrile (9) (1.168 g, 5.84 mmol) is added to a mixture of thionyl chloride (19.6 ml) and sulfuryl chloride (6 mL), and the resultant mixture is heated to about 60° C. for about 15 hours. The reaction mixture is then cooled to room temperature and the volatiles are removed in vacuo to provide a brown solid. Water (25 mL) is added to the brown solid and the resultant mixture is cooled to about 0° C., whereupon the pH of the mixture is adjusted to about 6.8 with 1N NaOH. The solid obtained is filtered to provide 6-[(Dichloromethylene)amino]-7-methyl-1H-benzimidazole-4-carbonitrile (38) (0.903 g, 61% Yield).

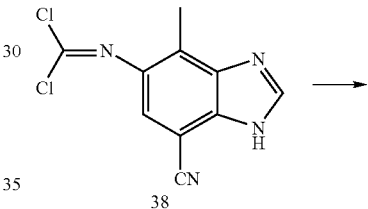

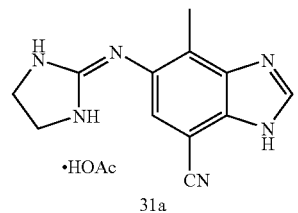

Preparation of 6-[(4,5-Dihydro-1H-imidazol-2-yl)amino-]-7-methyl-1H-benzimidazole-4-carbonitrile, Acetic Acid Salt (1:1) (31a)

A mixture of 6-[(Dichloromethylene)amino]-7-methyl-1H-benzimidazole-4-carbonitrile (38) (0.827 g, 3.28 mmol) and acetonitrile (25 mL) is cooled to 0° C., whereupon a solution of ethylenediamine (0.26 mL) in acetonitrile (2 mL) is slowly added. The mixture is then allowed to warm to ambient temperature and allowed to stir for about 12 hours. The volatiles are removed from the mixture in vacuo. Methanol (2 mL) and water (15 mL) are added to the residue, and 6N aqueous NaOH is added until a pH of 9 is attained. The solids that form are filtered and washed with water (2 mL). The solid is then-suspended in a mixture of methanol (17 mL) and acetic acid (0.2 mL) and stirred for 30 minutes. The mixture is then filtered. The methanol is then distilled off from the resulting filtrate, at atmospheric pressure, as acetonitrile (17 mL) is added. The resulting mixture is allowed to cool to ambient temperature, and is then cooled to 0° C. and held at this temperature for about 30 minutes. The solids that form are filtered, washed with acetonitrile (1 mL) and dried to provide 6-[(4,5-Dihydro-1H-imidazol-2-yl)amino-]-7-methyl-1H-benzimidazole-4-carbonitrile, acetic acid salt (1:1) (31a) (0.42 g, 43% Yield), as an off-white solid.

Example 18

Comparative Solubility Salt Data.

One skilled in the art could use a variety of techniques to ascertain the following solubilities in water at ambient temperature of the following salt forms of 6-[(4,5-Dihydro-1H-imidazol-2-yl)amino-]-7-methyl-1H-benzimidazole-4-carbonitrile—

| Free Base Form | about 0.4 mg/mL |
|---|---|
| Sulfate Salt Form | about 4 mg/mL |
| Acetate Salt Form | about 135 mg/mL |

One such technique is to prepare a saturated solution of the salt form by shaking a suspension of the salt form in water, until a saturated solution is obtained. The saturated solution is then centrifuged and the concentration of the supernatant is determined by quantitative HPLC analysis. A suitable HPLC method is described in Example 1.

Example 19

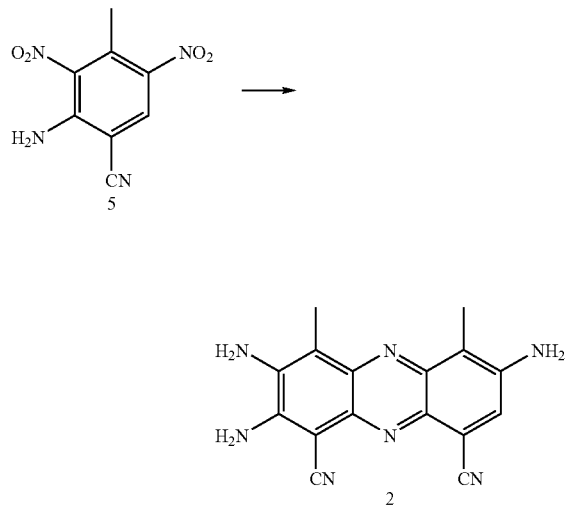

Synthesis of 2,3,7-Triamino-4,6-dimethyl-1,9-phenazinedicarbonitrile (2)

A mixture of 4-methyl-3,5-dinitrobenzonitrile (5) (50 g, 0.225 mmol), 5% palladium on carbon (10.0 g of 50% wet) and acetonitrile (400 ml) is hydrogenated under a hydrogen atmosphere (about 40 psi) at a temperature of about 30° C. for about 5 hours. The mixture is then filtered through a bed of Celite and the filter cake is washed with acetonitrile (about 200 mL). To a portion (about 400 mL) of the resulting solution is added water (about 400 mL) and the pH of the resulting mixture is adjusted to about 4.9 with 6N aqueous hydrochloric acid. The resulting mixture is then heated to about 40° C. and a stream of air is bubbled through the solution for about 18 hours. The pH of the resulting mixture is then adjusted again to about 5 with 6N aqueous hydrochloric acid and the temperature is held at about 40° C. for about another 2 hours. The mixture is then cooled to ambient temperature and the resulting solid is filtered, washed with water (500 mL), acetonitrile (200 mL) and dried to provide 2,3,7-triamino-4,6-dimethyl-1,9-phenazinedicarbonitrile (2) (19.44 g, about 85% Yield), as a dark red solid.

IX. Miscellaneous

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising 6-[(4,5-dihydro-IH-imidazol-2-yl)amino-]-7-methyl-1H-benzimidazole-4-carbonitrile, substantially free of 2,3,7-triamino-4,6-dimethyl-1,9-phenazinedicarbonitrile, or tautomer thereof.

2. The composition of claim 1, wherein the concentration of 2,3,7-triamino-4,6-dimethyl-1,9-phenazine-dicarbonitrile is less than 70 parts per billion.

3. The composition of claim 2, wherein the concentration of 2,3,7-triamino-4,6-dimethyl-1,9-phenazine-dicarbonitrile is less than 5 parts per billion.

4. The composition of claim 1 in the form of anhydrous monoacetate salt.

* * * * *